United States Patent
Lee

(10) Patent No.: US 9,237,869 B1
(45) Date of Patent: Jan. 19, 2016

(54) LAPEL ADAPTER FOR PHYSIOLOGICAL SENSOR POD

(71) Applicant: Salutron, Inc., Fremont, CA (US)

(72) Inventor: Yong Jin Lee, Seoul (KR)

(73) Assignee: SALUTRON, INC., Fremont, CA (US)

( * ) Notice: Subject to any disclaimer, the term of this patent is extended or adjusted under 35 U.S.C. 154(b) by 0 days.

(21) Appl. No.: 14/661,896

(22) Filed: Mar. 18, 2015

Related U.S. Application Data

(60) Provisional application No. 62/099,931, filed on Jan. 5, 2015.

(51) Int. Cl.
*G01D 11/24* (2006.01)
*G01D 11/30* (2006.01)
*A61B 5/00* (2006.01)

(52) U.S. Cl.
CPC .................................. *A61B 5/6804* (2013.01)

(58) Field of Classification Search
CPC ............................... G01D 11/24; G01D 11/30
USPC ............................................................ 73/431
See application file for complete search history.

(56) References Cited

U.S. PATENT DOCUMENTS

| | | | |
|---|---|---|---|
| 2012/0078071 A1* | 3/2012 | Bohm | G06F 1/3203 600/345 |
| 2015/0067811 A1* | 3/2015 | Agnew | H04L 63/0807 726/9 |

* cited by examiner

*Primary Examiner* — Lisa Caputo
*Assistant Examiner* — Jamel Williams
(74) *Attorney, Agent, or Firm* — Vierra Magen Marcus LLP

(57) ABSTRACT

Described herein is a lapel adaptor for use with a physiologic sensor pod having a housing including a top surface, a bottom surface, a peripheral surface, a groove extending around the peripheral surface, and a pair of electrodes spaced apart from one another on the bottom surface. The lapel adaptor includes a first portion comprising an elastic ring including an opening having an inner circumference slightly smaller than an outer circumference of the groove extending around the peripheral surface of the sensor pod housing. The lapel adaptor also includes a second portion having a pair of magnets spaced apart from one another by substantially a same distance as a distance between the pair of electrodes on the bottom surface of the sensor pod housing. The lapel adaptor further includes a third portion that enables the first and second portions of the lapel adaptor to be folded toward one another.

20 Claims, 19 Drawing Sheets

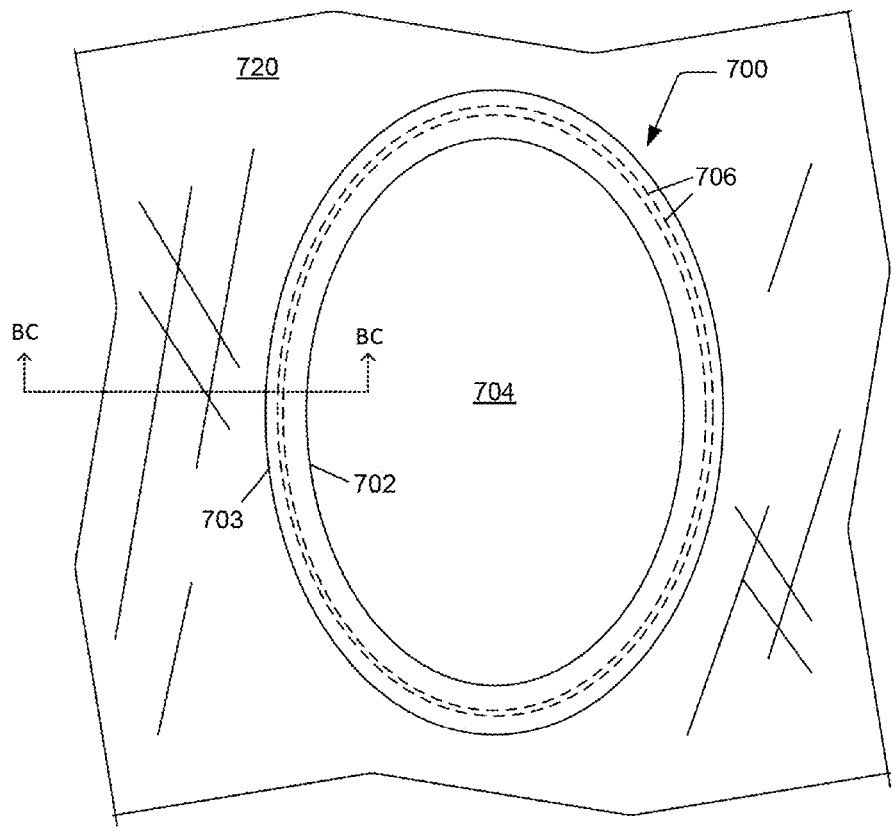
FIG. 7A
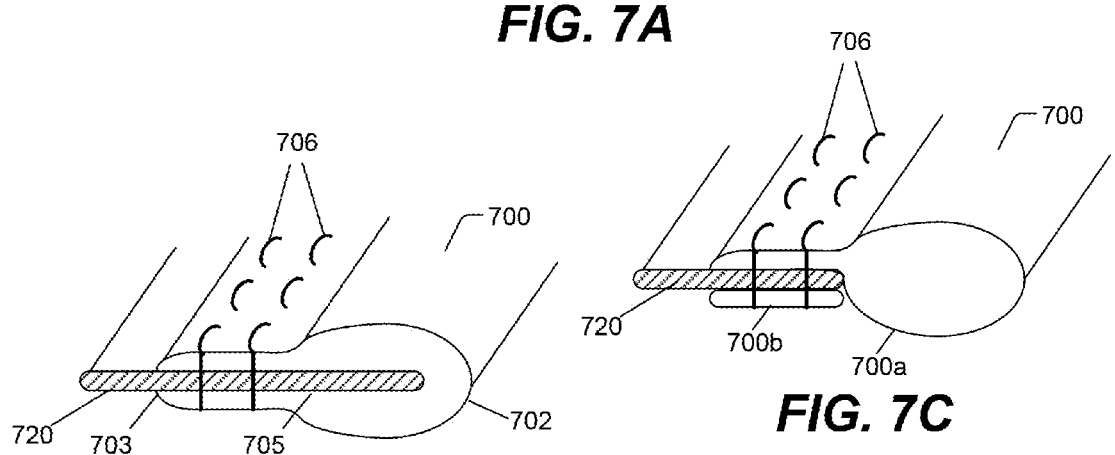
FIG. 7B
FIG. 7C

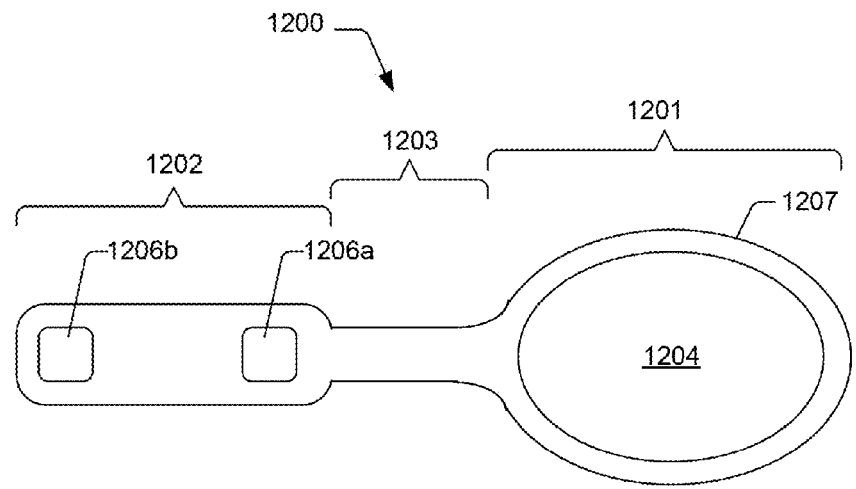
FIG. 12A
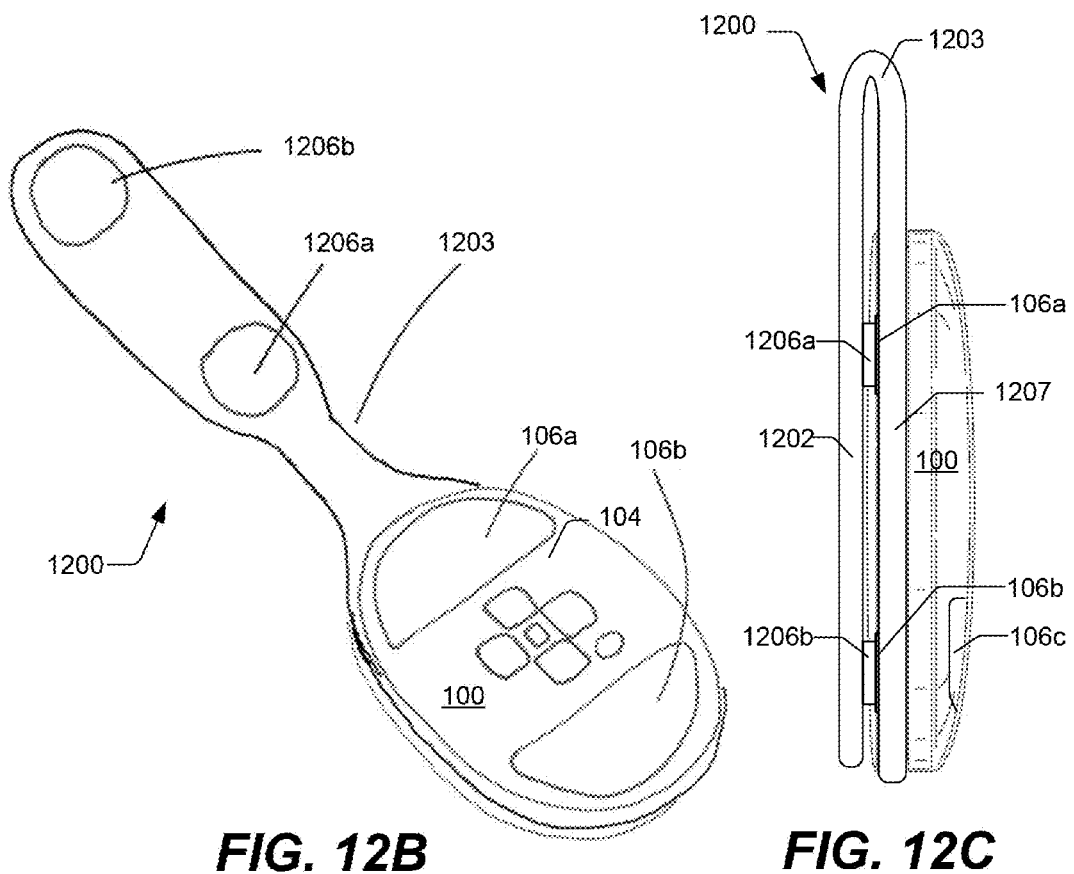
FIG. 12B  FIG. 12C

US 9,237,869 B1

LAPEL ADAPTER FOR PHYSIOLOGICAL SENSOR POD

PRIORITY CLAIM

This application claims priority to U.S. Provisional Patent Application No. 62/099,931, filed Jan. 5, 2015, which is incorporated herein by reference.

BRIEF DESCRIPTION OF THE DRAWINGS

FIGS. 7A, 7B and 7C illustrate an elastic ring that can be attached to an article of apparel or clothing, and used to selectively attach a sensor pod to the article of apparel or clothing, according to an embodiment.

FIGS. 12A, 12B and 12C illustrates a lapel adaptor that is configured to be selectively attached with or to the sensor pod, introduced in FIGS. 1A, 1B and 1C, to enable the sensor pod to be clipped to a lapel, a shirt pocket, a pant pocket, or the like.

DETAILED DESCRIPTION

Figure 1A:
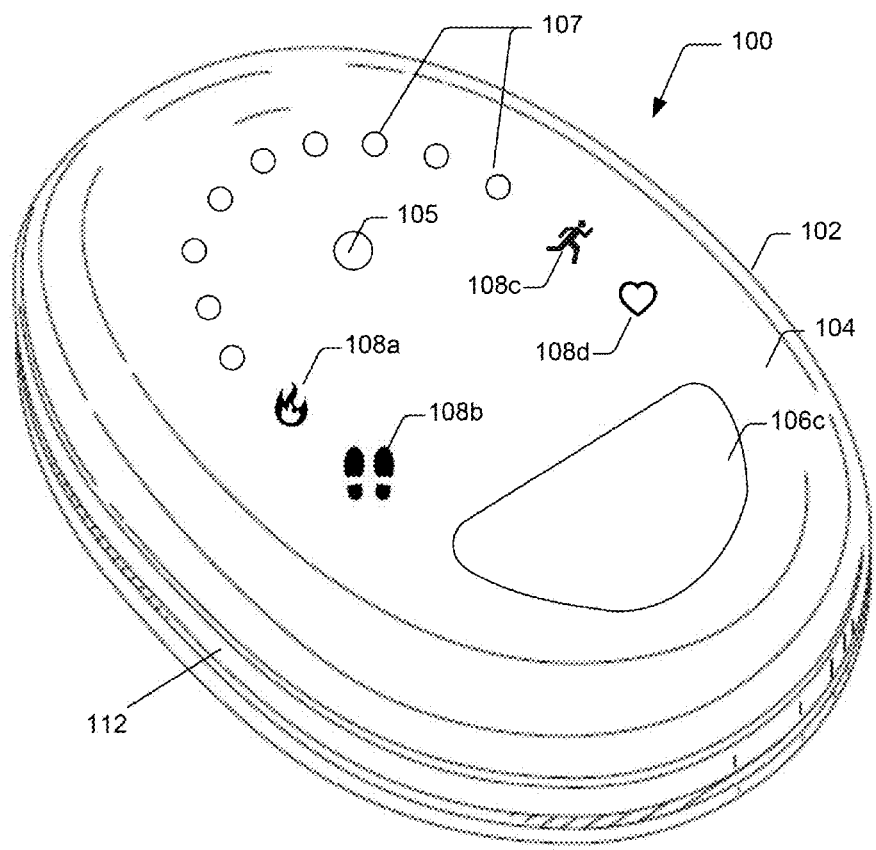
FIGS. 1A, 1B and 1C are, respectively, perspective, side and rear views of a physiological sensor pod according to an embodiment of the present technology.

In the following detailed description, reference is made to the accompanying drawings that form a part hereof, and in which is shown by way of illustration specific illustrative embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

Figure 1B:
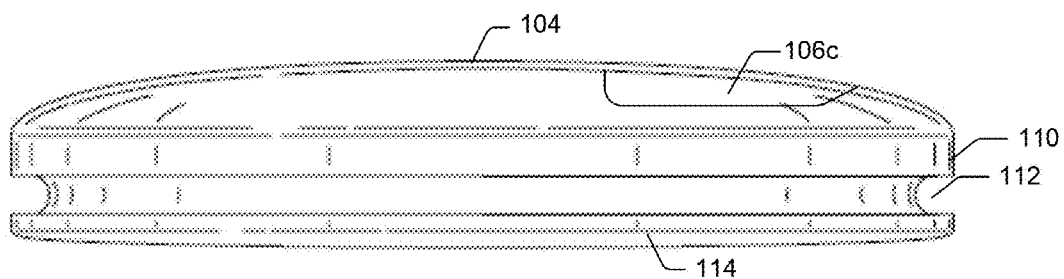
Figure 1C:
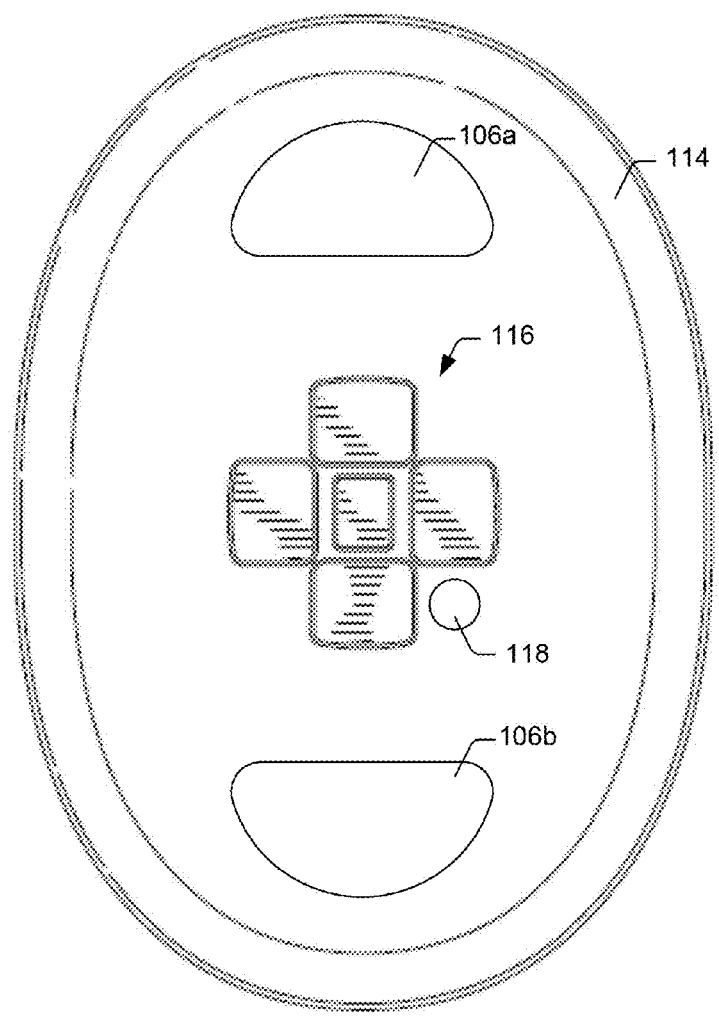

FIGS. 1A, 1B and 1C are, respectively, perspective, side and rear views of a physiological sensor pod 100 according to an embodiment of the present technology. The physiologic sensor pod 100 can be more succinctly referred to as a sensor pod 100, or can be referred to more generally as a sensor device 100, a user-wearable device 100, or simply a device 100. The sensor pod 100 is shown as including a housing 102 having a top surface 104, a bottom surface 114 and a peripheral surface 110 extending between the top surface 104 and the button surface 114. The housing 102 also includes a groove 112 within and extending about the peripheral surface 110. A battery, and electronic circuitry, including, but not limited to, a processor, memory, a wireless interface, switch circuitry, and a battery charging unit are located within the housing 102, as will be described in additional detail below. A majority of the housing 102 can be made of a plastic, a carbon composite, aluminum or some other metal, but is not limited thereto.

Where one or more light emitting elements and/or one or more light detectors are located within the housing 102, and the material of which a majority of the housing 102 is made is not light transmissive, the housing can include light transmissive windows (e.g., made of a clear or other light transmissive material) that allows light to enter and/or exit through the housing windows. The housing 102 can be made in two parts (e.g., a top part and a bottom part) that are connected together to encase the battery and electronic circuitry of the sensor pod 100. Where the housing 102 is made in two parts, the two parts can be primarily made of the same material, or of different materials.

In accordance with specific embodiments, the sensor pod 100 can wirelessly communicate with a base station (e.g., 352 in FIG. 3), which can be a mobile phone, a tablet computer, a personal data assistant (PDA), a laptop computer, a desktop computer, or some other computing device that is capable of performing wireless communication. More specifically, the sensor pod can include a wireless interface that enables it to communicate with and sync with a base station. The base station can, e.g., include a health and fitness software application and/or other applications, which can be referred to as apps. The sensor pod 100 can upload data obtained by the sensor pod 100 to the base station, so that such data can be used by a health and fitness software application and/or other apps stored on and executed by the base station.

Referring specifically to FIG. 1A, the top surface 104 of the housing 102 includes a top electrode 106c. In the embodiment shown, the top surface 104 of the housing 102 includes a goal indicator 107, which is shown as comprising a plurality of individually activateable light emitting elements arranged in a semicircle. The light emitting elements of the goal indicator 107 are preferably located within the housing 102, but are viewable through the top surface 104 of the housing 102. The top surface 104 of the housing 102 further includes a plurality of mode indicator icons 108a, 108b, 108c and 108d, which are used to indicate the present operational mode of the sensor pod 100. The mode indicator icons are shown as including a calories burned icon 108a, a walking icon 108b, a running icon 108c and a heart icon 108d. Light emitting elements within the housing 102, below the mode indicator icons 108a, 108b, 108c and 108d, can selectively emit light to illuminate one of the icons to indicate the mode in which the sensor pod 100 is operating. A user, through use of a base station (e.g., 352 in FIG. 3), can select the mode, or the sensor pod 100 or base station may select the mode based on data obtained from various sensors, algorithms, apps and/or the like. Although not shown, the housing 102 of the sensor pod 100 can optionally include a digital display that can be used, e.g., to display the time, date, day of the week and/or the like, and can also be used to display activity and/or physiological metrics, such as, but not limited to, heart rate (HR), heart rate variability (HRV), calories burned, steps taken, distance walked and/or run, and/or sleep metrics.

The housing 102, and more generally the sensor pod 100, can optionally also include an outward facing ambient light sensor (ALS) 105, which can be used to detect ambient light, and thus, can be useful for detecting whether it is daytime or nighttime, as well as for other purposes. Where the sensor pod 100 includes an ALS 105, the ALS can be placed behind a light transmissive window in the upper surface of the housing 102. Such an ALS 105 can include one or more photodetector, each of which can be a photoresistor, photodiode, phototransistor, photodarlington or avalanche photodiode, but is not limited thereto.

Referring now to FIG. 1C, the bottom surface 114 of the housing 102 is shown as including a pair of spaced apart electrodes 106a and 106b, and plurality of light transmissive windows 116 for one or more light emitting elements and one or more light detecting elements of a photoplethysmography (PPG) sensor, discussed in more detail below. Additionally, the bottom surface of the housing 102 is shown as including a thermally conductive metal contact 118 for a skin temperature sensor, also discussed in more detail below. The thermally conductive metal contact 118 can be made of aluminum or copper, but is not limited thereto. Exemplary electrical components and modules that can be included within the housing 102 of the sensor pod 100 are shown in and described below with reference to FIG. 3.

In accordance with an embodiment, the housing 102 is water tight and water proof, or at least water resistant. More generally, the sensor pod 100 is water tight or water resistant so that it can get wet and still operate. In accordance with an embodiment, to increase a probability that the sensor pod 100 remains water tight, the sensor pod 100 is designed such that once it is manufactured its housing 102 is not intended to be opened. For example, the housing 102 can be hermetically sealed. Accordingly, in such an embodiment the battery (e.g., 310 in FIGS. 3 and 4) is not replaceable, but rather, is only rechargeable. This also means that the battery cannot be temporarily removed and replaced to reset the sensor pod 100 in the event that the sensor pod 100 gets stuck in an operational loop, crashes or otherwise malfunctions. Further, to increase a probability that the sensor pod 100 remains water tight, in accordance with an embodiment there is/are no actionable buttons on the sensor pod 100. In such an embodiment, there is no button on the sensor pod 100 that can be used to reset the sensor pod 100 if it gets stuck in an operational loop, crashes or otherwise malfunctions. Accordingly, in accordance with an embodiment, a reset button (e.g., 540 in FIGS. 5A and 5B) is instead located on a charging unit (e.g., 500 in FIGS. 5A and 5B) that is used to charge the battery (e.g., 310 in FIGS. 3 and 4) of the sensor pod 100, and the sensor pod 100 is configured to detect when the reset button on the charging unit is activated, as will be described in additional detail below with reference to FIGS. 5A, 5B and 6.

Figure 2A:
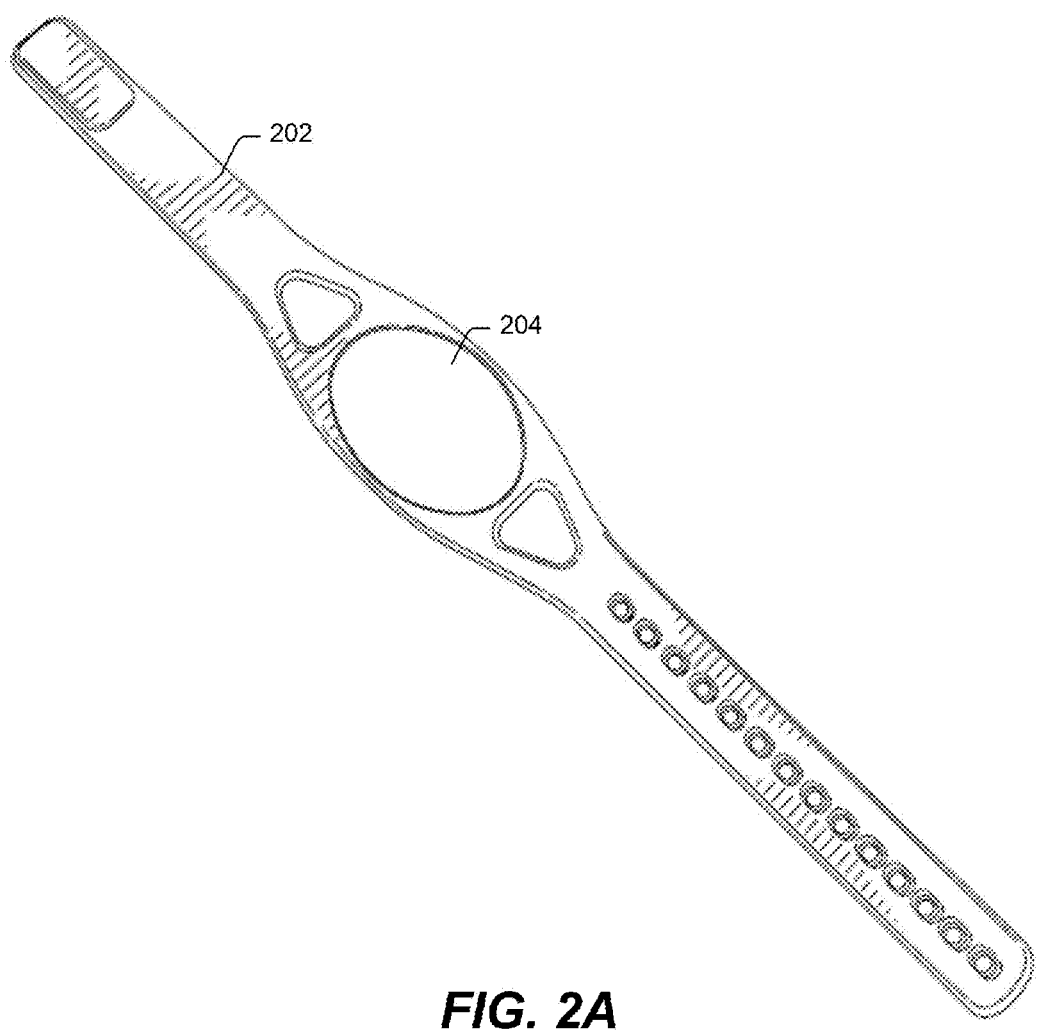
FIG. 2A illustrates a wrist band including an opening into which the physiological sensor pod introduced in FIGS. 1A, 1B and 1C can be inserted.
Figure 2B:
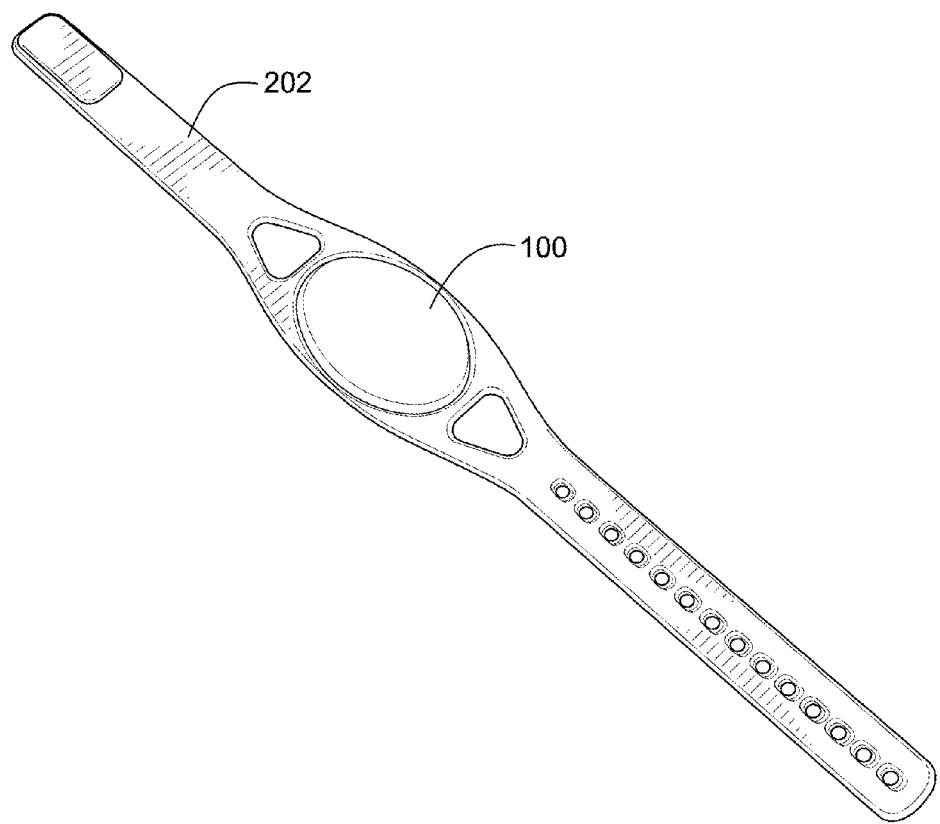
FIG. 2B illustrates the wrist band of FIG. 2A with the sensor pod introduced in FIGS. 1A, 1B and 1C inserted within the opening of the wrist band.

FIG. 2A illustrates a wrist band 202 that includes an opening 204 into which the groove 112 of the sensor pod 100 fits to secure sensor pod 100 in place. FIG. 2B illustrates the wrist band 202 with the sensor pod 100 secured within the opening 204. The sensor pod 100 can alternatively be placed in a similar opening in a chest strap, headband, swim cap, arm band, or some other user wearable band, strap, article of apparel or device. For example, a chest strap that is intended to strap the sensor pod 100 to a person's chest may resemble the wrist band 202 shown in FIGS. 2A and 2B, but would be longer in length to enable the strap to fit around a person's chest. In still other embodiments, the sensor pod 100 can be placed into a pocket within a sock or tight fitting shirt (e.g., a bicycle shirt) or other article of apparel or clothing that includes a pocket for the sensor pod. Such a pocket can include an opening that enables the backside of the sensor pod, which includes windows for a PPG or other optical sensor, electrodes or other sensor elements, to contact the wearer's skin to thereby enable the sensor(s) to operate properly. The opening in the pocket can also enable the groove 112 in the sensor pod 100 to be snapped into a correct position and held in place against a user's skin. The sensor pod 100 can alternatively be placed in an opening, slot and/or pocket in a helmet (e.g., a bicycle, motorcycle, skateboard, football, baseball, hockey, snowboard or ski helmet) or other headwear (e.g., a beanie, a baseball cap or any other type of hat). The sensor pod 100 may alternatively be placed in an opening, slot and/or pocket in a pair of glasses or a head mounted display (HMD) that positions the back surface 114 of the sensor pod 100 against a user's temple.

Figure 3:
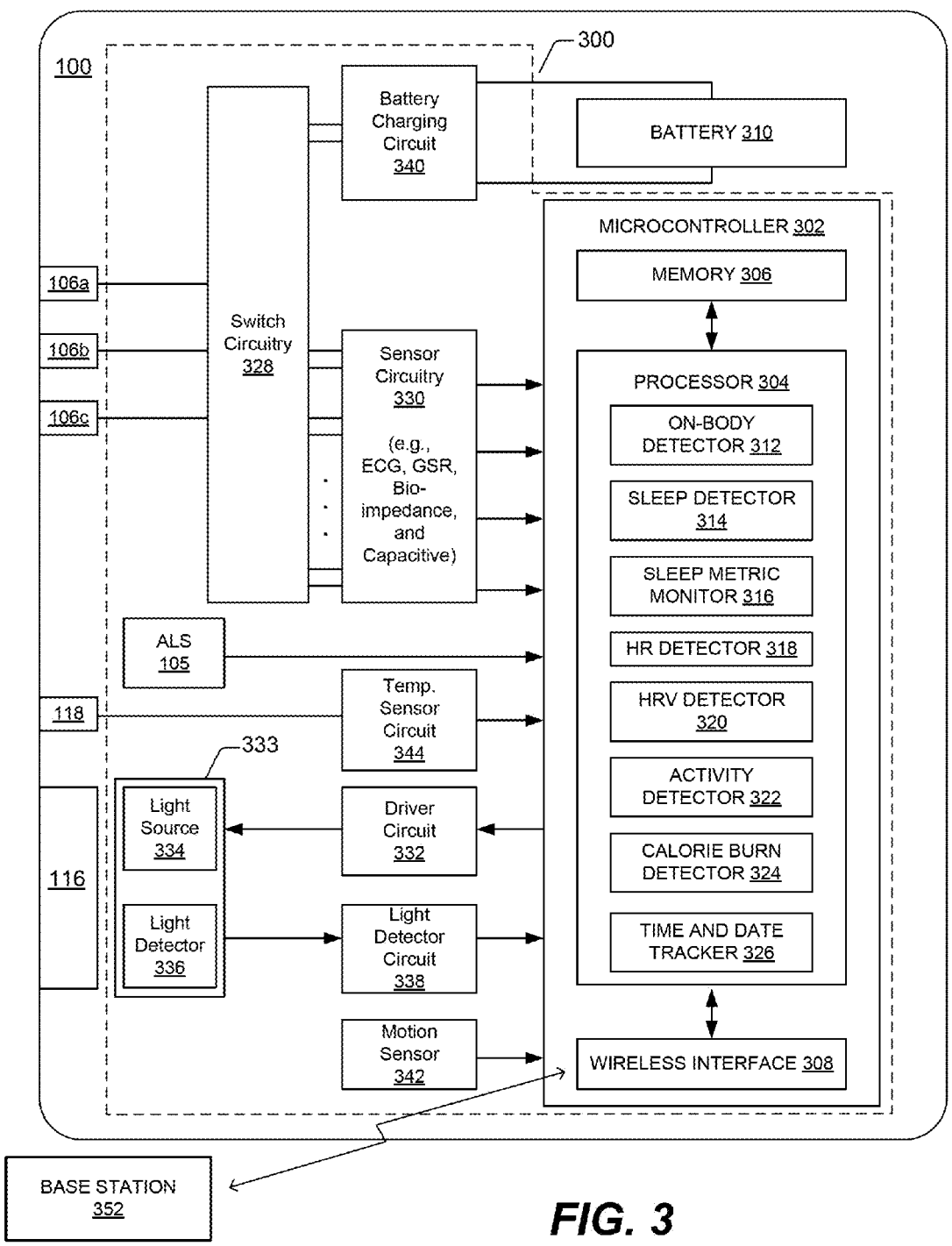
FIG. 3 depicts an example block diagram of electrical components that are located within the housing of the physiological sensor pod introduced in FIGS. 1A, 1B and 1C, according to an embodiment.

FIG. 3 depicts a block diagram of electrical components 300 of the sensor pod 100, according to an embodiment, which are located within the housing 102 of the sensor pod 100. More specifically, the components within the dashed block labeled 300 are exemplary electrical components of the sensor pod 100, which are powered by the battery 310. Referring to FIG. 3, the sensor pod 100 is shown as including a microcontroller 302 that includes a processor 304, memory 306 and a wireless interface 308. It is also possible that the memory 306 and wireless interface 308, or portions thereof, are external the microcontroller 302. Other electronic components 300 of the sensor pod 100 can include, but are not limited to, a battery charging circuit 340, sensor circuitry 330, a temperature sensor circuit 344, a driver circuit 332, a light detector circuit 338, a motion sensor 342, a photoplethysmography (PPG) sensor 333 and the optional ALS 105. It is also possible that electronic components 300 include more or less components than shown. The battery 310 is used to power the various components of the sensor pod, and a battery charger circuit 340 is used to charge the battery 310. While not specifically shown, the sensor pod 100 can also include one or more voltage regulators that are used to step-up and or step-down the voltage provided by the battery 310 to appropriate levels to power the various components of the sensor pod 100. The microcontroller 302, or the processor 304 thereof, receives signals from the various sensors and sensor circuits, or more generally, from the various circuitry.

At the left in FIG. 3 are small rectangular blocks that schematically represent the electrodes 106a, 106b and 106c and the temperature sensor contact 118, introduced above in the discussion on FIGS. 1A and 1C. The electrodes 106a, 106b and 106c can be referred to collectively as electrodes 106, or individually as an electrode 106. For simplicity, in FIG. 3 the electrode 106c is shown as being next to the electrodes 106a and 106b. However, as can be appreciated from FIGS. 1A and 1C, the electrode 106c is remotely located relative to the electrodes 106a and 106b. More specifically, the electrodes 106a and 106b are located on the bottom surface 114 of the housing 102, as shown in FIG. 1C, and the electrode 106c is located on the top surface 104 of the housing 102, as shown in FIG. 1A. Alternatively, the electrode 106c can be located on an upper portion of the peripheral surface 110 of the housing 102, so long as it does interfere with the groove 112 and is accessible (e.g., can be touched by a user's finger) when the sensor pod 100 is inserted within an opening in a wrist band (e.g., 202 in FIGS. 2A and 2B), chest band or other apparel that enables a user to wear the sensor pod 100. More generally, FIG. 3 is not intended to show the precise locations of the various sensors, electrodes, contact, electrical components, windows, etc. of the sensor pod 100.

Also shown at the left in FIG. 3 is a block representing the window(s) 116 for a light source 334 and a light detector 336 of a photoplethysmography (PPG) sensor 333. The PPG sensor 333 includes the light source 334 that is driven by a driver circuit 332, and the light detector 336 whose output is provided to a light detector circuit 338. The driver circuit 332 can be controlled by the microcontroller 302 or the processor 304 thereof. The driver circuit 332 can include, e.g., a current source and a switch that selectively provides the current produced by the current source to the light source 304. An output of the light detector circuit 338 can be provided to the microcontroller 302 or the processor 304 thereof. The light source 334 can include one or more light emitting elements, each of which can be a light emitting diode (LED), incandescent lamp or laser diode, but is not limited thereto. While it is preferred that the light source 334 emit infrared (IR) light, because the human eye cannot detect IR light, the light source 334 can alternatively produce light of other wavelengths. The light detector 336 can include one or more photodetectors (also referred to as light detecting elements), each of which can be a photoresistor, photodiode, phototransistor, photodarlington or avalanche photodiode, but is not limited thereto. In accordance with an embodiment, the light source 334 includes a single IR LED, and the light detector 336 includes four photodiodes arranged around the single IR LED. For example, referring briefly back to FIG. 1C, the center one of the windows 116 can allow light to be emitted by the single IR LED, and the four other windows 116 surrounding the center window can allow reflected/scattered light to be incident of the four photodiodes that surround the single IR LED.

Referring again to FIG. 3, the light source 334 is selectively driven by the driver circuit 332 to emit light. When the light source 334 emits light a portion of the emitted light is reflected or backscattered by patient tissue, and reflected/backscattered light is received by the light detector 336. In this manner, changes in reflected light intensity are detected by the light detector 336, which outputs a PPG signal indicative of the changes in detected light, which are indicative of changes in blood volume. The light detector circuit 338 can, e.g., convert the PPG signal output by the light detector 336 from a current signal to a voltage signal, and filter and/or amplify the PPG signal. Additionally, the PPG signal can be converted to a digital signal using an analog-to-digital converter (ADC), if the PPG signal is to be analyzed in the digital domain. Such an ADC can be part of the light detector circuit 338, part of the microcontroller 302, are independent thereof. Each cardiac cycle in the PPG signal generally appears as a peak, thereby enabling the PPG signal to be used to detect peak-to-peak intervals, which can be used to calculate heart rate (HR) and heart rate variability (HRV). In accordance with certain embodiments, the light source 334 emits light of two different wavelengths that enables non-invasive monitoring of arterial oxygen saturation using pulse oximetry techniques.

The sensor pod 100 is also shown as including a motion sensor 342. In accordance with an embodiment the motion sensor 342 is an accelerometer. The accelerometer can be a three-axis accelerometer, which is also known as a three-dimensional (3D) accelerometer, but is not limited thereto. The accelerometer may provide an analog output signal representing acceleration in one or more directions. For example, the accelerometer can provide a measure of acceleration with respect to x, y and z axes. The motion sensor 342 can alternatively be a gyrometer, which provides a measure of angular velocity with respect to x, y and z axes. It is also possible that the motion sensor 342 is an inclinometer, which provides a measure of pitch, roll and yaw that correspond to rotation angles around x, y and z axes. It is also possible the sensor pod 100 includes multiple different types of motion sensors, some examples of which were just described. Depending upon the type(s) of motion sensor(s) used, such a sensor can be used to detect the posture of a portion of a user's body (e.g., a wrist or chest) on which the sensor pod 100 is being worn. The output(s) of the motion sensor 342 can be provided to the microcontroller 302 or the processor 304 thereof.

A block labeled sensor circuitry 330 is used to generally refer to the various sensor circuits (discussed in more detail below) that can be selectively connected, by switch circuitry 328, to various different combinations of the electrodes 106a, 106b and 106c. For example, as will be described in more detail below with reference to FIG. 4, the sensor circuitry 330 can include one or more electrocardiogram (ECG) sensor circuit, a bioimpedance analysis (BIA) sensor circuit, and a capacitive sensor circuit, but is not limited thereto. The temperature sensor contact 118 is shown as being connected to the temperature sensor circuit 344.

The wireless interface 308 can wireless communicate with a base station (e.g., 352), which as mentioned above, can be a mobile phone, a tablet computer, a PDA, a laptop computer, a desktop computer, or some other computing device that is capable of performing wireless communication. The wireless interface 308, and more generally the sensor pod 100, can communicate with a base station 352 using various different protocols and technologies, such as, but not limited to, Bluetooth™, Wi-Fi, ZigBee or ultrawideband (UWB) communication. In accordance with an embodiment, the wireless interface 308 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a base station 352.

Figure 4:
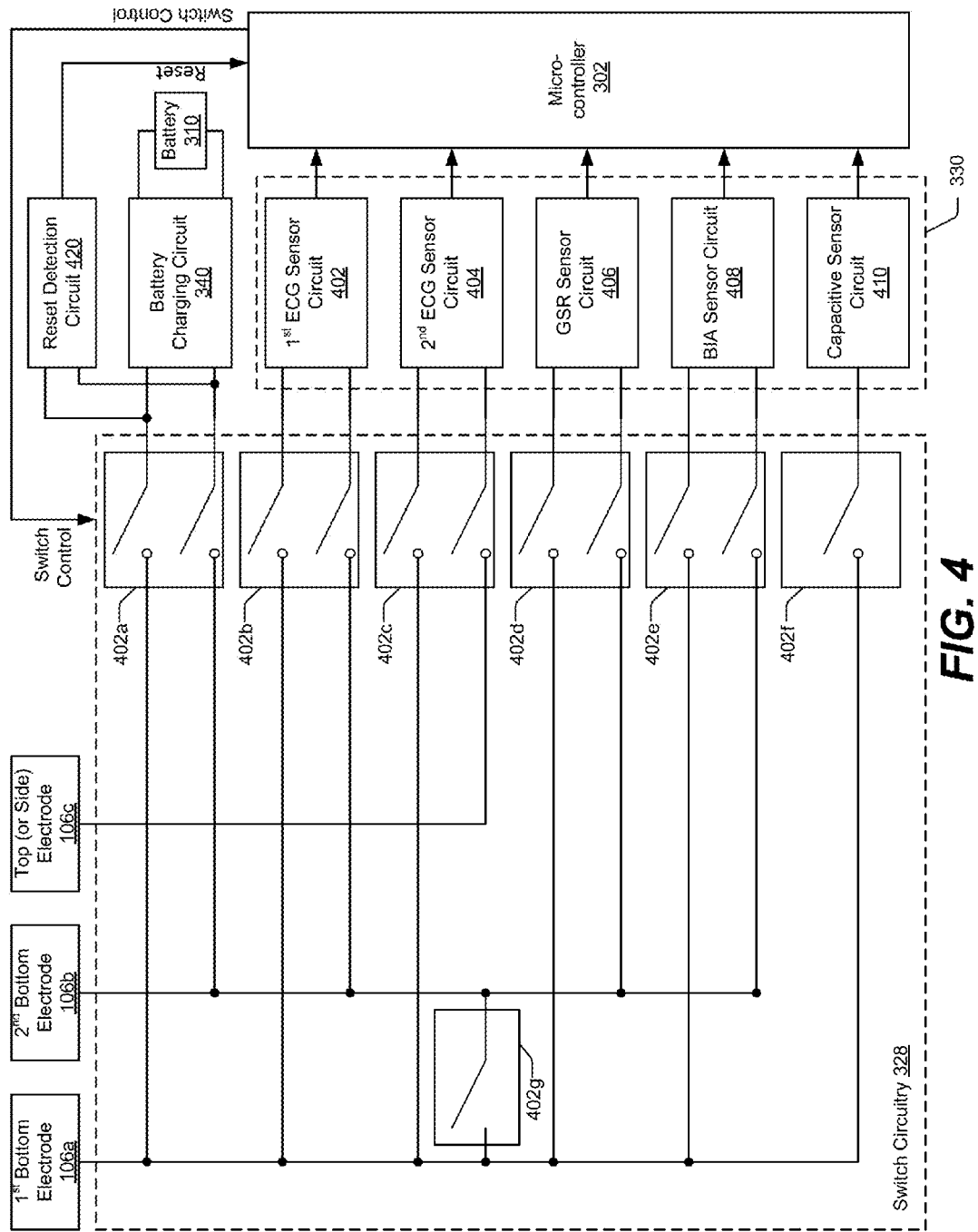
FIG. 4 illustrates additional details of the switch circuitry and sensor circuitry introduced in FIG. 3, according to an embodiment.

FIG. 4 will now be used to describe additional details of the switch circuitry 328 and sensor circuitry 330 introduced in FIG. 3. Referring to FIG. 4, the sense circuitry 330 is shown as including a 1st ECG sensor circuit 402, a 2nd ECG sensor circuit 404, a galvanic skin resistance (GSR) sensor circuit 406, a bioimpedance analysis (BIA) sensor circuit 408 and a capacitive sensor circuit 410. As can be appreciated from FIG. 4, the switch circuitry 328 enables these various sensor circuits, of the sensor circuitry 330, to share the same electrodes 106. In an embodiment, the microcontroller 302 (or some other controller) produces one or more switch control signals that selectively control how and when individual ones (or subsets of) the electrodes 106 is/are connected to the various inputs of the sensor circuits 402, 404, 406, 408 and 410. As can also be appreciated from FIG. 4, the switch circuitry 328 can be used to selectively connect the two bottom electrodes 106a and 106b to the battery charging circuit 340. More generally, the switch circuitry 328 enables two (or more) of the same electrodes 106 to be used, albeit at different times, by the battery charging circuit 340 and one or more sensor circuits (e.g., 402, 404, 406, 408 and/or 410). Also shown in FIG. 4 is a reset detection circuit 420, additional details of which are discussed below with reference to FIG. 6.

In FIG. 4, the switch circuitry 328 is schematically shown as including switches 402a, 402b, 402c, 402d, 402e, 402f and 402g. The switches can be implemented using transistor types of switches, but are not limited thereto. For example, in accordance with an embodiment, the switches 402a are implemented using reed switches.

When the switches 402a are closed, also referred to as activated, the electrodes 106a and 106b are connected to the battery charging circuit 340. When the switches 402b are closed, the electrodes 106a and 106b are connected to the $1^{st}$ ECG sensor circuit 402. The $1^{st}$ ECG sensor circuit 402 is used to sense an ECG signal between the two bottom electrodes 106a and 106b when the electrodes 106a and 106b are contact with a person's chest. When the two bottom electrodes 106a and 106b of the sensor pod 100 are against another portion of a person's body (e.g., a person's wrist), instead of against a person's chest, an ECG signal cannot be sensed between the two bottom electrodes 106a and 106b.

When the switches 402c are closed, the electrodes 106a and 106c are connected to the $2^{nd}$ ECG sensor circuit 402. The $2^{nd}$ ECG sensor circuit 404 is used to sense an ECG signal between at least one of the bottom electrodes 106a, 106b that is in contact with a person's skin (e.g., on their wrist) and the top (or side) electrode 106c that is in contact with another portion of the person's skin (e.g., a finger on the opposite hand). In other words, an ECG signal can be sensed when one (or both) of the electrodes 106a, 106b are in contact with a user's arm (or other body part) and the electrode 106c is in contact with a user's finger on their other arm, in which case a circuit is completed that extends across the user's chest cavity that includes their heart.

While the $2^{nd}$ ECG sensor circuit 404 is being used, both of the bottom electrodes 106a and 106b can be shorted to one another by the switch 402g (such that they function as one large electrode) and connected to one input of the $2^{nd}$ ECG sensor circuit 404, while the other input of the $2^{nd}$ ECG sensor circuit 404 is connected to the top (or side) electrode 106c. Alternatively, while the $2^{nd}$ ECG sensor circuit 404 is being used, only one of the bottom electrodes 106a or 106b is connected to one input of the $2^{nd}$ ECG sensor circuit 404, while the other input of the $2^{nd}$ ECG sensor circuit 404 is connected to the top (or side) electrode 106c. In other words, one of the bottom electrodes 106a or 106b may not be connected the $2^{nd}$ ECG sensor circuit 404. More specifically, while the switches 402c are closed, the switch 402g can optionally also be closed, in which case the electrodes 106a and 106b are shorted (i.e., connected) together and function as one larger single electrode.

The $1^{st}$ and $2^{nd}$ ECG sensor circuits 402 and 404 can each include one or more low power, precision amplifiers with programmable gain and/or automatic gain control, bandpass filtering, and a threshold detection circuit, as known in the art, to selectively sense an ECG signal of interest. In an embodiment, the maximum gain provided by the $2^{nd}$ ECG sensor circuit 402 is greater than the maximum gain provided the $1^{st}$ ECG sensor circuit 404. In accordance with an embodiment, the $1^{st}$ and $2^{nd}$ ECG sensor circuits 402 and 404 share at least some circuitry. In an embodiment, there is only one ECG sensor circuit that is used regardless of whether an ECG signal is being sensed between the two bottom electrodes 106a and 106b, or between one (or both) of the bottom electrodes 106a, 106b and the top (or side) electrode 106c. In the embodiment where there is only one ECG sensor circuit, the switch circuitry 328 connects each of the bottom electrodes 106a and 106b to a different one of the two inputs of the ECG sensor circuit when the sensor pod 100 is placed against a person's chest; and the switch circuitry 328 connects the one (or both) of the bottom electrodes 106a, 106b to the one of the inputs of the ECG sensor circuit, and connects the top (or side) electrode 106c to the other input of the ECG sensor circuit, when the sensor pod 100 is placed against another portion of the user's body, besides their chest, such as on a person's wrist.

When the switches 402d are closed, the electrodes 106a and 106b are connected to the GSR sensor circuit 406. The GSR sensor circuit 406 is used to senses a galvanic skin resistance between a pair of the electrode 106 (e.g., the electrodes 106a and 106b) that are in contact with a person's skin. The galvanic skin resistance measurement will be relatively low when a user is wearing the sensor pod 100 such that the electrodes 106a and 106b are against their skin. By contrast, the galvanic skin resistance measurement will be very high when the electrodes 106a and 106b are not in contact with the user's skin. The galvanic skin resistance measurement, which can also be referred to as a galvanic skin response, may also vary based on levels perspiration.

When the switches 402e are closed, the electrodes 106a and 106b are connected to the BIA sensor circuit 408. The BIA sensor circuit 408 is used to measure impedance, at one or more frequencies, between a pair of the electrodes 106 (e.g., the electrodes 106a and 106b) that are in contact with a person's skin.

When the switch 402f is closed, the electrode 106a is connected to the capacitive sensor circuit 410. The switch 402g can also be closed, in which case the electrodes 106a and 106b are shorted together and are connected to the capacitive sensor circuit 410. The capacitive sensor circuit 420 is used to measure a capacitance between one (or both) of the electrode 106a, 106 and a person's skin, which information can be used, e.g., to determine whether or not the sensor pod 100 is in contact with a person's skin. In accordance with an embodiment, one (or both) of the electrode 106a, 106 function as one plate of a capacitor, while an object (e.g., a user's wrist or chest) functions as the other plate of the capacitor. The capacitive sensor circuit 420 can indirectly measure capacitance, and thus proximity, e.g., by adjusting the frequency of an oscillator in dependence on the proximity of an object relative to the electrode(s) 106 connected to the capacitive sensor circuit 420, or by varying the level of coupling or attenuation of an AC signal in dependence on the proximity of an object relative the electrode(s) 106 connected to the capacitive sensor circuit 420.

In accordance with an embodiment, the switches 402a are implemented as switches that are normally closed, while the other switches (e.g., the switches 402b-402g) are implemented as switches that are normally open. By having the switches 402a be normally closed, the electrodes 106a and 106b are by default connected to the battery charging circuit 340. This way, if a voltage generated by the battery 310 drops so low that it cannot provide sufficient power to the microcontroller 302 (or another switch controller) to control the switch circuitry 328, then the sensor pod 100 is in a state that the battery 310 can be charged. More generally, the switch circuitry 328 is, by default, in a configuration that connects the electrodes 106a and 106b to the battery charging circuit 340, so that if an energy level of the battery 310 is insufficient to power the microcontroller 302 and/or the switch circuitry 328 the battery 310 can still be charged using a charging unit (e.g., 500 in FIGS. 5A and 5B).

As mentioned above, in accordance with an embodiment the switches 402a that are used to selectively connect the electrodes 106a and 106b to the battery charging circuit 340 are implemented as reed switches. A reed switch is an electrical switch operated by a magnetic field. In other words, the switches 402a can be magnetically actuated reed switches. Where the switches 402a are implemented as reed switches, the reed switches can be open in their default state, and physically located within the sensor pod 100 such that when the sensor pod 100 is sitting on/against the charging unit (e.g., 500 in FIGS. 5A and 5B) one or more magnets (e.g., 516a and 516b in FIGS. 5A and 5B) of the charging unit cause the reed switches to switch to a closed (i.e., activated) state, which causes the electrodes 106a and 106b of the sensor pod 100 to be connected to the battery charging circuit 340 of the sensor pod 100. In other words, referring briefly to FIGS. 5A and 5B, when the sensor pod 100 is placed on/against the charging unit 500, the magnet(s) 516a and/or 516b can cause the switches 402a, implemented as reed switches, to connect the electrodes 106a and 106b to the battery charging circuit 340 so that the battery 310 can be charged.

Referring again to FIG. 3, the sensor pod 100 is shown as including various detectors or trackers, including an on-body detector 312, a sleep detector 314, a sleep metric detector 316, a heart rate (HR) detector 318, a heart rate variability (HRV) detector 320, an activity detector 322, a calorie burn detector 324 and a time and date tracker 326. The various detectors and trackers may communicate with one another, as will be explained below. Each of these detectors and trackers 312, 314, 316, 318, 320, 322, 324 and 326 can be implemented using software, firmware and/or hardware. It is also possible that some of these detectors and trackers are implemented using software and/or firmware, with others implemented using hardware. Other variations are also possible. In accordance with a specific embodiments, each of these detectors or trackers 312, 314, 316, 318, 320, 322, 324 and 326 is implemented using software code that is stored in the memory 306 and is executed by the processor 304. The memory 306 is an example of a tangible computer-readable storage apparatus or memory having computer-readable software embodied thereon for programming a processor (e.g., 304) to perform a method. For example, non-volatile memory can be used. Volatile memory such as a working memory of the processor 304 can also be used. The computer-readable storage apparatus may be non-transitory and exclude a propagating signal.

The on-body detector 312 uses signals and/or data obtained from one or more of the above described sensors and/or sensor circuits to determine whether the sensor pod 100 is being worn by a user (also referred to herein as a person). For example, the on-body detector 312 can use signals/and/or data obtained from the light source 334 and light detector 336 (which can collectively be referred to as a PPG sensor 333), the GSR sensor circuit 406, the temperature sensor circuit 344, the capacitive sensor circuit 410 and/or the motion sensor 342 to determine whether the sensor pod 100 is being worn by a user. The on-body detector 312 can be used to selective operate the sensor pod 100 in a low power mode when the on-body detector 312 detects that the sensor pod 100 is not being worn by a user. Additional details of the on-body detector 212 are described in U.S. patent application Ser. No. 14/341,248, titled "User-Wearable Devices with Power Conserving Features," which was filed Jul. 24, 2014.

The sleep detector 314 uses signals and/or data obtained from one or more of the above described sensors to determine whether a user, who is wearing the sensor pod 100, is sleeping. For example, signals and/or data obtained using the motion sensor 342 can be used to determine when a user is sleeping. This is because people typically move around less when sleeping compared to when awake. For another example, if the sensor pod 100 includes an outward facing ambient light sensor (ALS) (e.g., 105 in FIG. 1A) then signals and/or data obtained using the outward facing ALS can additionally or alternatively be used to determine when a user is sleeping. This is because people typically sleep in a relatively dark environment with low levels of ambient light. Additionally, if the user's arm posture can be detected from the motion sensor 342, then information about arm posture can also be used to detect whether or not a user is sleeping. The sleep detector 314 can also be used to detect when a user, who is wearing the sensor pod 100, wakes up, as well as when the user is awake.

The sleep metric detector 316 uses signals and/or data obtained from one or more of the above described sensors and/or other detectors and trackers to quantify metrics of sleep, such as total sleep time, sleep efficiency, number of awakenings, and estimates of the length or percentage of time within different sleep states, including, for example, rapid eye movement (REM) and non-REM states. The sleep metric detector 316 can, for example, use signals and/or data obtained from the motion sensor 342 and/or from the HR detector 318 to distinguish between the onset of sleep, non-REM sleep, REM sleep and the user waking from sleep. One or more quality metric of the user's sleep can then be determined based on an amount of time a user spent in the different phases of sleep. Such quality metrics can be uploaded to a base station (e.g., 352) for display and/or further analysis. Additionally, or alternatively, if the sensor pod 100 included a digital display, such metrics can be displayed on such a digital display.

The HR detector 318 can use signals and/or data obtained from the PPG sensor 333 to detect HR. For example, the PPG sensor 333 can be used to obtain a PPG signal from which peak-to-peak intervals can be detected, which can also be referred to as beat-to-beat intervals. Additionally, or alternatively, beat-to-beat intervals can be determined from an ECG signal obtained using an ECG sensor circuit (e.g., 402 or 404 in FIG. 4) by measuring the time interval between R-waves or other features of the ECG signal. The beat-to-beat intervals, which are intervals between heart beats, can be converted to HR using the equation HR=(1/beat-to-beat interval)*60. Thus, if the beat-to-beat interval=1 sec, then HR=60 beats per minute (bpm); or if the beat-to-beat interval=0.6 sec, then HR=100 bpm. In an embodiment, the HR detector 318 can measure the beat-to-beat intervals of a PPG signal, and also measure the beat-to-beat intervals of an ECG signal, and use an average of the two types of beat-to-beat intervals to detect HR. In another embodiment, there can be a determination of whether a PPG signal or an ECG signal has a greater to signal-to-noise ratio (SNR), and which ever one of the PPG and ECG signals has a greater SNR can be used by the HR detector 318 to detect HR. The user's HR can be uploaded to a base station (e.g., 352) for display and/or further analysis. Additionally, or alternatively, if the sensor pod 100 included a digital display, HR or information indicative can be displayed on such a digital display.

The HRV detector 320 can use signals and/or data obtained from the PPG sensor 333 and/or one of the ECG sensor circuits 402 or 404 to detect HRV. For example, in the same manner as was explained above, beat-to-beat intervals can be determined from a PPG signal obtained using the PPG sensor 333. Additionally, or alternatively, beat-to-beat intervals can be determined from an ECG signal obtained using an ECG sensor circuit (e.g., 402 or 404 in FIG. 4) by measuring the time interval between R-waves or other features of the ECG signal. HRV can be determined by calculating a measure of variance, such as, but not limited to, the standard deviation (SD), the root mean square of successive differences (RMSSD), or the standard deviation of successive differences (SDSD) of a plurality of consecutive beat-to-beat intervals. Alternatively, or additionally, an obtained PPG signal and/or ECG signal can be converted from the time domain to the frequency domain, and HRV can be determined using well known frequency domain techniques. In an embodiment, the HRV detector 320 can measure the beat-to-beat intervals of a PPG signal, and also measure the beat-to-beat intervals of an ECG signal, and use an average of the two types of beat-to-beat intervals to detect HRV. In another embodiment, there can be a determination of whether a PPG signal or an ECG signal has a greater to signal-to-noise ratio (SNR), and which ever one of the PPG and ECG signals has a greater SNR can be used by the HRV detector 320 to detect HRV. The user's HRV can be uploaded to a base station (e.g., 352) for display and/or further analysis. Additionally, or alternatively, if the sensor pod 100 included a digital display, HRV or information indicative thereof can be displayed on such a digital display.

The activity detector 322 can determine a type and amount of activity of a user based on information such as, but not limited to, motion data obtained using the motion sensor 342, heart rate as determined by the HR detector 318, skin temperature as determined by the skin temperature sensor 340, and time of day. The activity detector 322 can use motion data, obtained using the motion sensor 342, to determine the number of steps that a user has taken with a specified amount of time (e.g., 24 hours), as well as to determine the distance that a user has walked and/or run within a specified amount of time. Activity metrics can be uploaded to a base station (e.g., 252) for display and/or further analysis. Additionally, or alternatively, if the sensor pod 100 included a digital display, such metrics can be displayed on such a digital display. The goal indicator 107, shown in FIG. 1A, can also be used to inform a user of how close they are to reaching an activity related goal, which can be a steps goal or a distance goal.

The calorie burn detector 324 can determine a current calorie burn rate and an amount of calories burned over a specified amount of time based on motion data obtained using the motion sensor 342, HR as determined using the HR detector 318, and/or skin temperature as determined using the skin temperature sensor 340. A calorie burn rate and/or an amount of calories burned can uploaded to a base station (e.g., 252) for display and/or further analysis. Additionally, or alternatively, if the sensor pod 100 included a digital display, such information can be displayed on such a digital display. The goal indicator 107, shown in FIG. 1A, can also be used to inform a user of how close they are to reaching a calories burned goal.

The time and date tracker 326 can keep track of the time of day, date, and/or the like. The time and date tracker 326 of the sensor pod 100 can be synced with a similar tracker of the base station 352. The time and data tracker 326 can provide time of day and date information to the other detectors described herein and/or can be used to date and/or time stamp collected data.

The sensor pod 100 can include less modules than shown in FIG. 3, more modules than show and/or alternative types of modules. For example, the sensor pod 100 can also include a body water content module and/or a body fat content module that calculates the user's body water content and/or body fat percentage based on measurements obtained using the BIA sensor circuit 408. Alternatively, the base station 352 can calculate body water content and/or body fat content based on data obtained using the BIA sensor circuit 408 of the sensor pod 100. For another example, the sensor pod 100 can include a stress module that estimates a user's stress level based on measures obtained using the GSR sensor circuit 406, one of the the ECG sensor circuits 402, 404 and/or the skin temperature sensor circuit 344. Alternatively, the base station 352 can estimate the user's stress level based on data obtained from the GSR sensor circuit 406, one of the the ECG sensor circuits 402, 404 and/or the skin temperature sensor circuit 344 of the sensor pod 100.

The sensor pod 100 can also include respiration module that determines respiration rate from a PPG signal obtained using the PPG sensor 333 and/or from the ECG signal obtained using an ECG sensor circuit 402 or 404. For another example, a blood pressure module can determine blood pressure from PPG and ECG signals by determining a metric of pulse wave velocity (PWV) and converting the metric of PWV to a metric of blood pressure. More specifically, a metric of PWV can be determining by determining a time from a specific feature (e.g., an R-wave) of an obtained ECG signal to a specific feature (e.g., a maximum upward slope, a maximum peak or a dicrotic notch) of a simultaneously obtained PPG signal. An equation can then be used to convert the metric of PWV to a metric of blood pressure. These are just a few examples of other types of modules or detectors that can be included within sensor pod 100, which are not intended to be all encompassing.

Referring again to FIG. 3, the microcontroller 302, or the processor 304 thereof, can determine which switches of the switch circuitry 328 to open and close based on which mode the sensor pod 100 is operating in. For example, when the sensor pod 100 is in a HR or HRV detection mode, and the sensor pod 100 is resting against a person's chest (such that the electrodes 106a and 106b are contacting the person's skin), the switches 402b can be closed. For another example, when the sensor pod 100 is in a HR or HRV detection mode, and the sensor pod 100 is strapped to a person's wrist (e.g., using the wrist band 202 in FIGS. 2A and 2B), then the switches 402c (and optionally also the switch 402g) can be closed. For still another example, when the sensor pod 100 is in a mode where galvanic skin resistance needs to be measured, then the switches 402c can be closed. The sensor pod 100 itself can decide when to change modes. Alternatively, or additionally, a base station (e.g., 352) in wireless communication with the sensor pod 100 can select which mode the sensor pod 100 is operating in. As mentioned above, in accordance with an embodiment, the switches 402a are normally closed, and the other switches are normally open, so that a default mode for the sensor pod 100 is a battery charging mode.

Figure 5A:
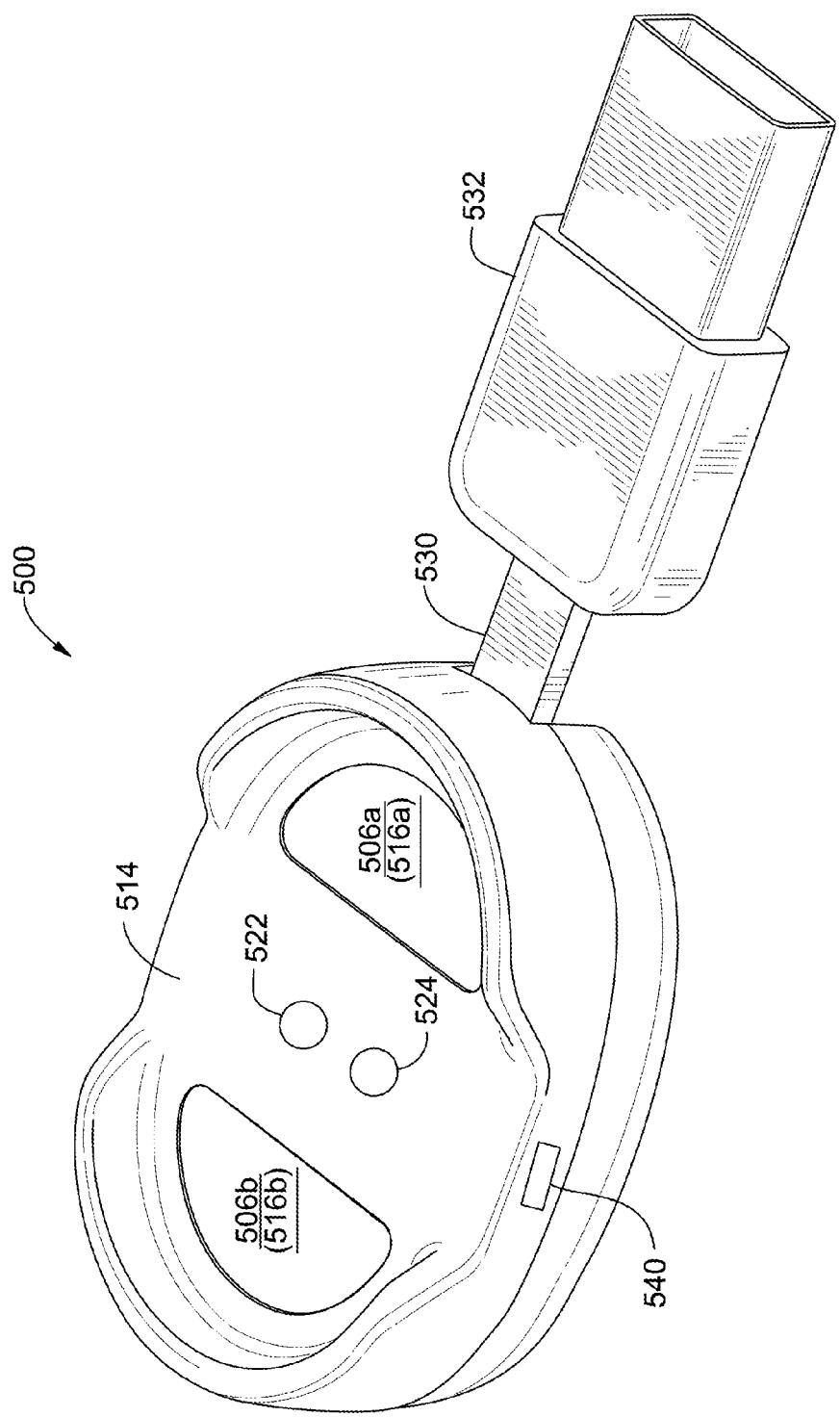
FIGS. 5A and 5B are, respectively, perspective and top views of the charging unit that is used to charge the sensor pod introduced in FIGS. 1A, 1B and 1C, according to an embodiment.
Figure 5B:
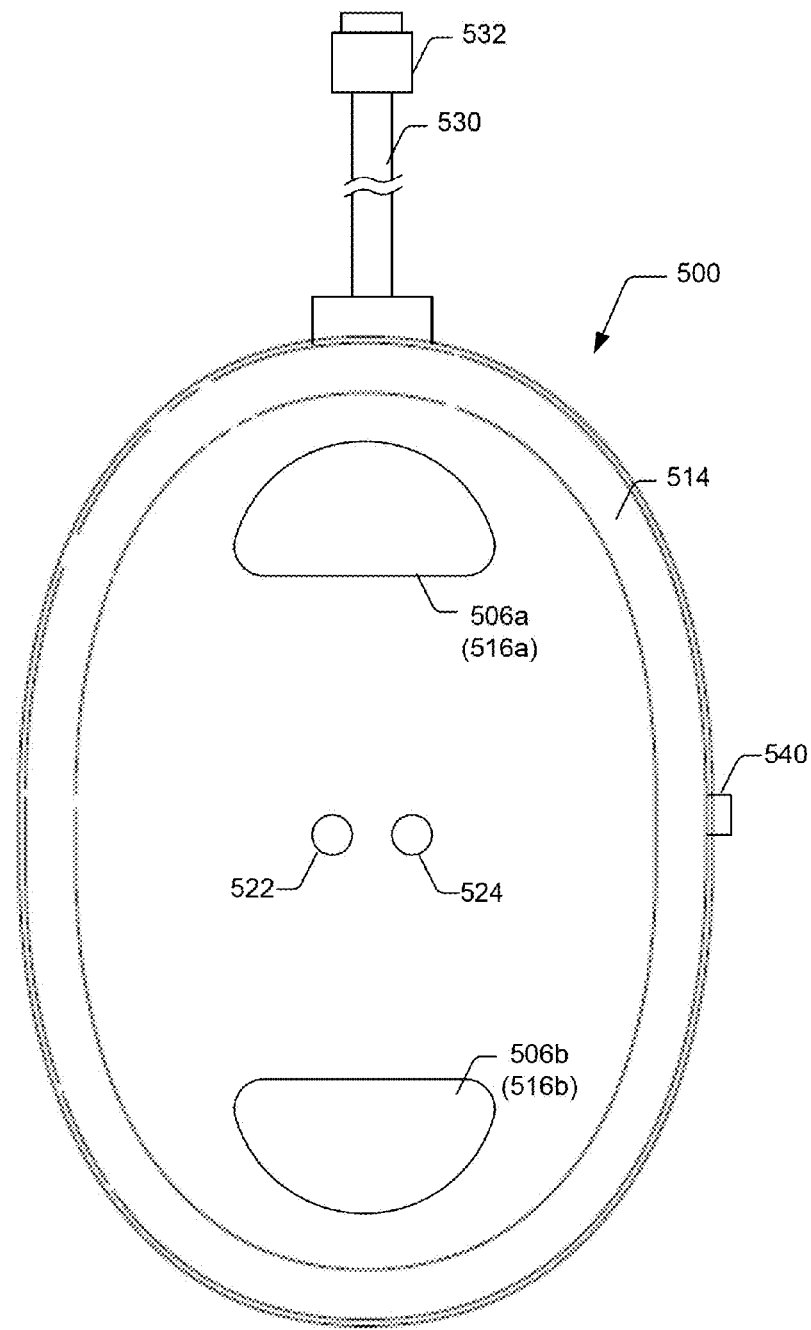

FIGS. 5A and 5B are, respectively, perspective and top views of a charging unit 500 that is used to charge the sensor pod 100 in accordance with an embodiment. The charging unit 500 is shown as including a housing 514 having a pair of electrical contacts 506a and 506b. The electrical contacts 506a and 506b are spaced apart from one another and are intended to be electrically coupled to the bottom electrodes 106a and 106b of the sensor pod 100, when the sensor pod 100 is placed upon the charging unit 500. A cable 530 that includes an adaptor 532 (e.g., a USB adaptor) that pluggable into a power source (e.g., a computing device) to provide power to the charging unit 500. The cable 530 can alternatively include a plug having prongs that can be plugged into an electrical wall socket to provide power to the charging unit. Other ways of providing power to the charging unit 500 are also possible and within the scope of embodiments described herein, as would be appreciated by one of ordinary skill in the art reading this description.

The charging unit 500 includes electrical circuitry within the housing 514 that generates a predetermined voltage (+/−a tolerance) between the electrical contacts 506a and 506b. When the electrical contacts 506a and 506b are in contact with the electrodes 106a and 106b of the sensor pod 100, the battery charging circuit 340 of the sensor pod 100 is powered by the charging unit 500 and the battery 310 of the sensor pod 100 is charged. Such powering of the battery charging circuit 340, through use of a direct contact electrical coupling between the electrical contacts 506a and 506b of the charging unit 500 and the battery charging circuitry 330 of the sensor pod 100, provides for faster and more efficient charging of the battery 310 than would be possible if there was instead an inductive coupling between the charging unit 500 and the battery charging circuitry 330 of the sensor pod 100.

In accordance with an embodiment, the electrical contacts 506a and 506b are magnetic. The electrical contacts 506a and 506b can themselves be magnetic, or more likely, a magnet 516a can be located below the electrical contact 506a and a magnet 516b can be located below the electrical contact 506b. Magnetizing the electrical contacts 506a and 506b (e.g., using adjacent magnets 516a and 516b) makes it easier for a person to correctly place the electrodes 106a and 106b of the sensor pod 100 against (e.g., on top of) the electrical contact 506a and 506b, and helps keep the electrodes 106a and 106b of the sensor pod 100 properly aligned with and against the electrical contact 506a and 506b during charging of the battery 310 of the sensor pod 100. The magnets 516a and 516b can be permanent magnets. Alternatively, the magnetic force of the magnets 516a and 516b can be generated using electricity, e.g., by generating an electromagnetic field.

In an embodiment, the charging unit 500 includes a light source 522 and a light detector 524, which collectively can operate as an optical proximity detector that is used to detect when the sensor pod 100 is resting on/against the charging unit 500. In accordance with an embodiment, the charging unit 500 only generates the predetermined voltage (+/−a tolerance) between its electrical contacts 506a and 506b when the charging unit detects that a sensor pod 100 is resting on and/or against the charging unit 500. There are various different techniques that the charging unit 500 can use to detect when that a sensor pod 100 is resting on/against the charging unit 500. In one embodiment, the light source 522 and the light detector 524 operate as an optical proximity sensor to detect whether or not a sensor pod 100 is resting on/against the charging unit 500. In other words, the charging unit 500 can utilize the light source 522 and the light detector 524, operating as an optical proximity detector, to detect when a sensor pod 100 is resting on/against the charging unit 500. The charging unit 500 can alternatively use other techniques to detect when a sensor pod 100 is resting on/against the charging unit 500 while also being within the scope of the embodiments described herein.

The charging unit 500 is also shown as including a reset button 540 that can be used to reset the sensor pod 100 while the sensor pod 100 is resting on/against the charging unit 500. The sensor pod 100 may need to be reset, e.g., if it gets stuck in an operational loop, crashes or otherwise malfunctions. While the reset button 540 is shown as being located on the side of the housing 514, the reset button 540 can be located at a myriad of other locations. Referring briefly back to FIG. 4, in accordance with an embodiment the reset detection circuit 420 detects when the rest button on the charging unit 500 is activated, and in response thereto, outputs a reset signal that is provided to a reset pin of the microcontroller 302 of the sensor pod 100. Additional details of the operation of the reset detection circuit 420, according to specific embodiments, are described below with reference to FIG. 6. The inclusion of a reset button 540 on the charging unit 500 is especially useful where the sensor pod 100 has no activatable buttons (and thus, no the sensor pod 100 has no reset button) and where the housing 102 of the sensor pod 100 is not intended to be opened (and thus, the sensor pod 100 cannot be reset by removing and replacing its battery 310 within its housing 102).

Figure 6:
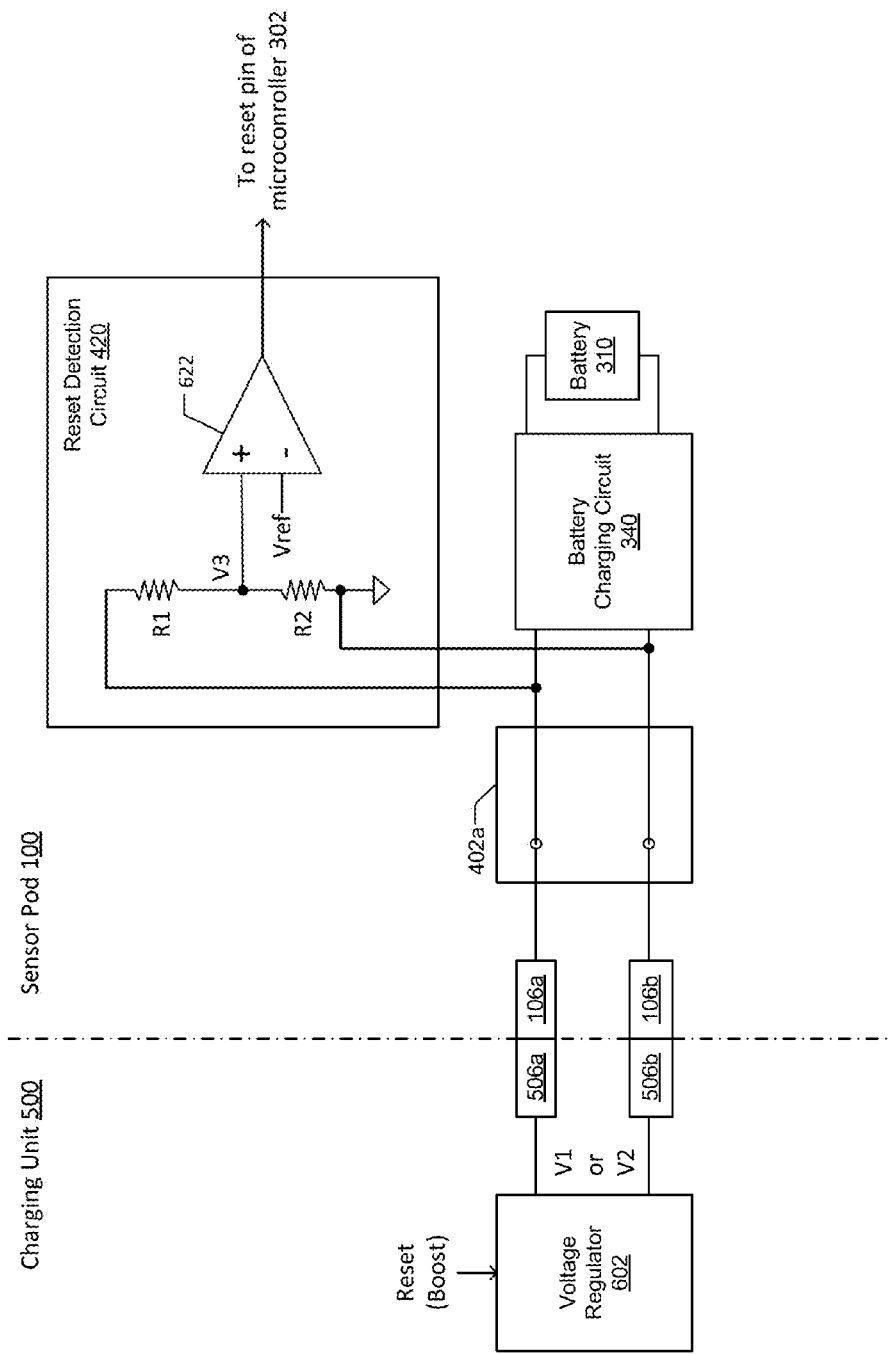
FIG. 6 provides details of a reset detection circuit of the sensor pod, according to an embodiment.

FIG. 6 provides details of a reset detection circuit 420 of the sensor pod 100 according to an embodiment. In FIG. 6, the components shown to the left of the vertical dashed line are components of the charging unit 500, and the components shown to the right of the vertical dashed line are components of the sensor pod 100. In FIG. 6, the electrodes 106a and 106b of the sensor pod 100 are shown as being in contact, respectively, with the electrical contacts 506a and 506b of the charging unit 500. The charging unit 500 is shown as including a voltage regulator 602 that generates a first output voltage V1 or a second output voltage V2, where V2 is greater than V1. In accordance with certain embodiments, V2 is at least 20% greater than V1, V2 is preferably at least 50% greater than V1, and even more preferably V2 is at least twice V1. In an embodiment, the voltage regulator 602 normally produces the first output voltage V1, which is the nominal voltage that is used by the battery charging circuit 340 to charge the battery 310. For example, the voltage V1 can be 3.3V, but is not limited thereto. In response to the reset button (e.g., 540 in FIGS. 5A and 5B) being pressed, the voltage regulator 602 generates the second output voltage V2, which can be, e.g., 8V, but is not limited thereto. Numerous other components can be included within the charging unit 500, such as, but not limited to, a DC-DC converter, or an AC-DC converter, one of which can provide a voltage input to the voltage regulator 602, as would be appreciated by one or ordinary skill in the art reading this disclosure.

In accordance with certain embodiments of the present technology, the reset detection circuit 420 is adapted to output a reset signal, which causes the sensor pod 100 to be reset, when a voltage between the electrodes 106a and 106b is greater than a reset threshold level. In the specific embodiment shown in FIG. 6, the reset detection circuit 420 is shown as including a comparator 622 that compares a voltage V3 to a reference voltage (Vref), wherein the voltage V3 is indicative of the voltage output by the voltage regulator 602, or more generally, is indicative of the voltage between the electrical contacts 506a and 506b of the charging unit 500. The voltage V3 can actually be equal to V1 or V2, are can be stepped down versions thereof produced using the resistors R1 and R2 and/or some other circuitry. The reference voltage (Vref) is indicative of the reset threshold level.

Still referring to FIG. 6, in accordance with an embodiment the output of the comparator 622, which will be either high or low, is the reset signal generated by the reset detection circuit 420. When the voltage V3 is less than Vref, then the output of the comparator 622 will be low. When the voltage V3 is greater the Vref, then the output of the comparator 622 will be high. In other words, the comparator 622 outputs the reset signal when the voltage V3 (indicative of the voltage between the electrodes 106a and 106b) is greater than the reference voltage (Vref) (indicative of the reset threshold level). Assuming the reset pin of the microcontroller 302 is active high, this means that when V3 is greater than Vref, the microcontroller 302 will be reset. More specifically, when the voltage output by the voltage regulator 602 is sufficiently high to cause the voltage V3 to exceed Vref, then the microcontroller 302, and more generally the sensor pod 100, will be reset. This is just one exemplary implementation of the reset detection circuit 420. For example, the inverting (−) and non-inverting (+) inputs of the comparator 622 can be swapped if the microcontroller 302 is instead adapted to be reset in response to a low input signal being provided to its reset pin. For another example, the voltage V3 provided to the comparator need not be generated using the resistors R1 and R2. Rather, in an alternative embodiment, one of the inputs of the comparator 622 can receive that actual voltage level (V1 or V2) provided by the charging unit 500 to the sensor pod 100. Other variations are also possible, as would be appreciated by one of ordinary skill in the art reading this disclosure. In such variations, the reset detection circuit 420 detects when the voltage provide by the charging unit 500 is above its nominal voltage level, and more specifically above a reset threshold level, and interprets such a detection as an indication that a reset signal should be generated to reset the sensor pod 100.

As explained above in the discussion of FIGS. 2A and 2B, the sensor pod 100 can be inserting into an opening 204 in a wrist band 202, or some other band or strap, such as a headband, arm band or some other user wearable band, strap or device. As also noted above, the sensor pod 100 can alternatively be placed into a pocket within a sock or tight fitting shirt (e.g., a bicycle shirt) or other article of apparel or clothing that includes a pocket for the sensor pod 100. Such a pocket can include an opening that enables the backside of the sensor pod 100, which includes windows for the PPG sensor (and/or other optical sensor(s)), electrodes and/or other sensor elements, to contact the wearer's skin to thereby enable the sensor(s) to operate properly. Such an opening can also enable the groove 112 in the sensor pod 100 to be snapped into a correct position and held in place against a user's skin. The sensor pod 100 can alternatively be placed in an opening, slot and/or pocket in a helmet (e.g., a bicycle, motorcycle, skateboard, football, baseball, hockey, snowboard or ski helmet) or other headwear (e.g., a beanie, a baseball cap or any other type of hat). The sensor pod 100 may alternatively be placed an opening, slot and/or pocket in a pair of glasses or a head mounted display (HMD) that positions the back surface 114 of the sensor pod 100 against a user's temple.

FIGS. 7A, 7B and 7C will now be used to explain in more detail how the sensor pod 100 can be selectively attached to an article of apparel or clothing. Referring to FIG. 7A, an elastic ring 700 is shown as being attached to piece of fabric 720 such that an opening in the fabric is aligned with an opening 704 in the elastic ring 700. The elastic ring 700 is shown as having oval or elliptical shape and generally has the same shape as the circumferential surface 110 of the sensor pod 100. In accordance with an embodiment, an inner circumference 702 of the elastic ring 700 is slightly smaller than the outer circumference of the groove 112 in the circumferential surface 110 of the sensor pod 100. This enables the groove 112 in the sensor pod 100 to be snapped into the opening 704 in the elastic ring 700 and held in place, e.g., against the skin of a user wearing the article of apparel or clothing that includes the piece of fabric 720. The elastic ring 700 can be sewn into the fabric 720 using stitches 706 made of thread or a similar material. While two rows of the stitches 706 are shown in FIGS. 7A, 7B and 7C, a single row of stitches can be used, or more than two rows of stitches can be used. The elastic ring 700 can be made of silicon, rubber, or some other similar elastic material.

FIG. 7B illustrates a perspective cross-sectional view of the elastic ring 700 along the dashed line BC-BC in FIG. 7A, according to an embodiment. Referring to FIG. 7B, a slit 705 extends from an outer circumference 703 of the elastic ring 700 toward, but not all the way to, the inner circumference 702 of the elastic ring 700. A portion of the fabric 720 is inserted into the slit 705 and then a peripheral portion of the elastic ring 700 is sewn, by the stitches 706, to the fabric 720. Additionally, or alternatively, an adhesive can be used to attach a portion of the fabric 720 within the slit 705.

FIG. 7C illustrates a perspective cross-sectional view of the elastic ring 700 along the dashed line BC-BC in FIG. 7A, according to another embodiment. Referring to FIG. 7C, the elastic ring 700 is shown as including two sub-components, including a main ring 700a and a support ring 700b. Both the main ring 700a and the support ring 700b can be made of silicon, rubber, or some other similar elastic material. Alternatively, the support ring 700b can be made of a more rigid material, since the support ring 700b does not need to be stretched. As can be appreciated from FIG. 7C, a portion of the fabric 720 is placed between a peripheral portion of the main ring 700a and the support ring 700b. The peripheral portion of the main ring 700a and the support ring 700b are stitched together with the portion of the fabric 720 therebetween to thereby attach the elastic ring 700 to the fabric 720.

Figure 8A:
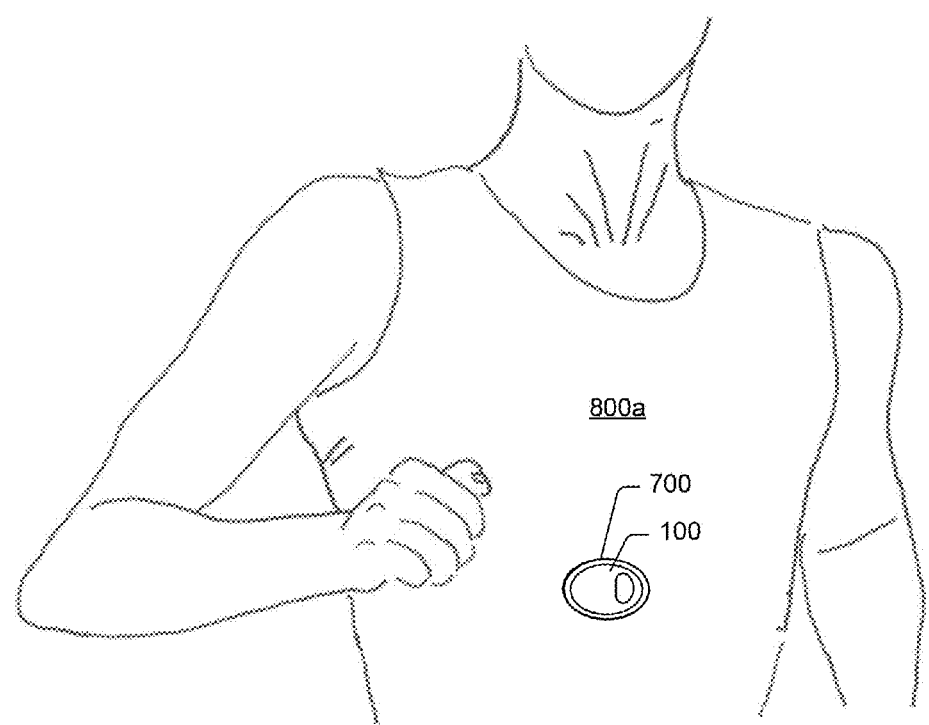
FIG. 8A illustrates the sensor pod, introduced in FIGS. 1A, 1B and 1C, attached to a tight fitting shirt, according to an embodiment.

FIG. 8A illustrates a tight fitting shirt 800a having an elastic ring 700 (described with reference to FIGS. 7A, 7B and 7C) attached thereto. FIG. 8A also shows the sensor pod 100 snapped into the elastic ring 700 and thereby selectively attached to the shirt 800a.

Figure 8B:
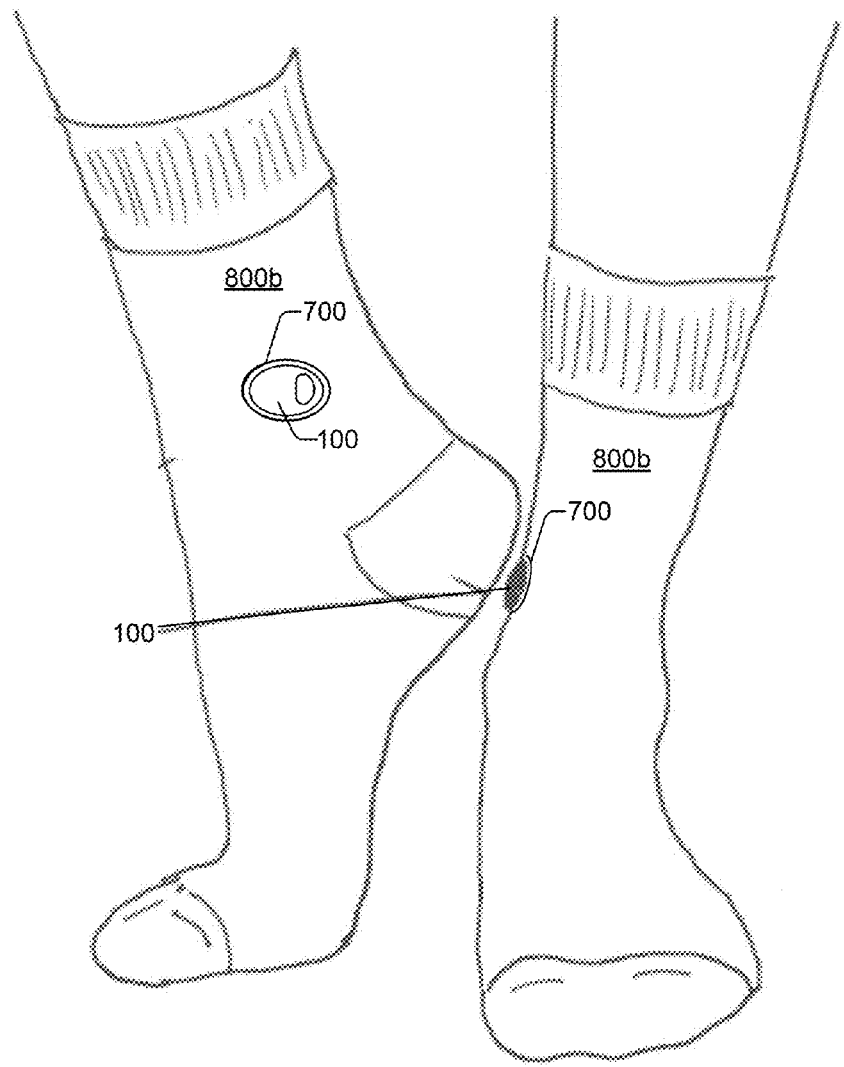
FIG. 8B illustrate two of the sensor pods, introduced in FIGS. 1A, 1B and 1C, attached to a pair of socks, according to an embodiment.

FIG. 8B illustrates a pair of socks 800b having an elastic ring 700 (described with reference to FIGS. 7A, 7B and 7C) attached thereto. FIG. 8B also shows one of the sensor pods 100 snapped into the elastic ring 700 in each of the socks 800b and thereby attached to the socks 800b.

Figure 8C:
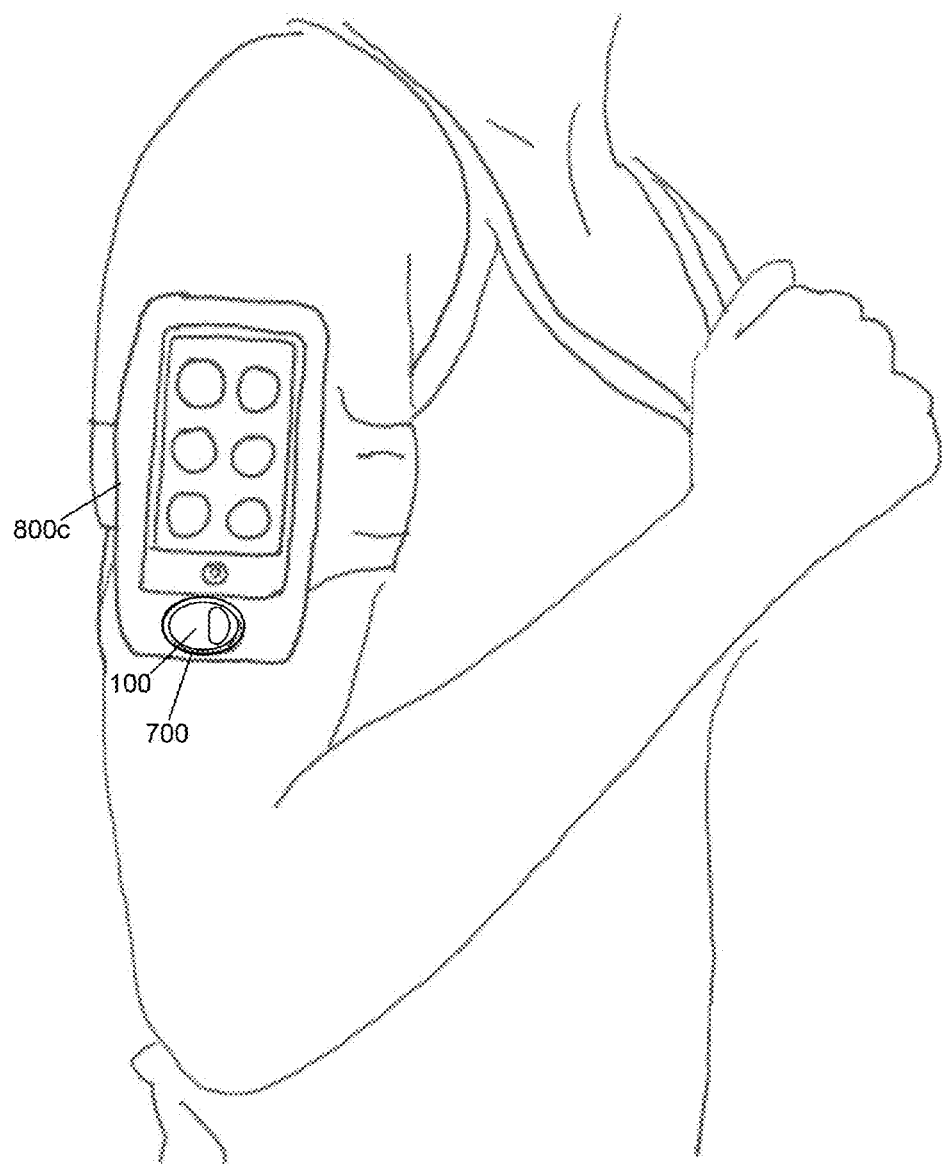
FIG. 8C illustrates the sensor pod(s), introduced in FIGS. 1A, 1B and 1C, attached to an arm band, according to an embodiment.

FIG. 8C illustrates an arm band 800c having an elastic ring 700 (described with reference to FIGS. 7A, 7B and 7C) attached thereto. FIG. 8C also shows one of the sensor pods 100 snapped into the elastic ring 700 in the arm band 800c and thereby attached to the arm band 800c. FIG. 8C further illustrates that the arm band 800c can also carry a mobile phone, which as explained above, may function as a base station for the sensor pod 100.

Figure 8D:
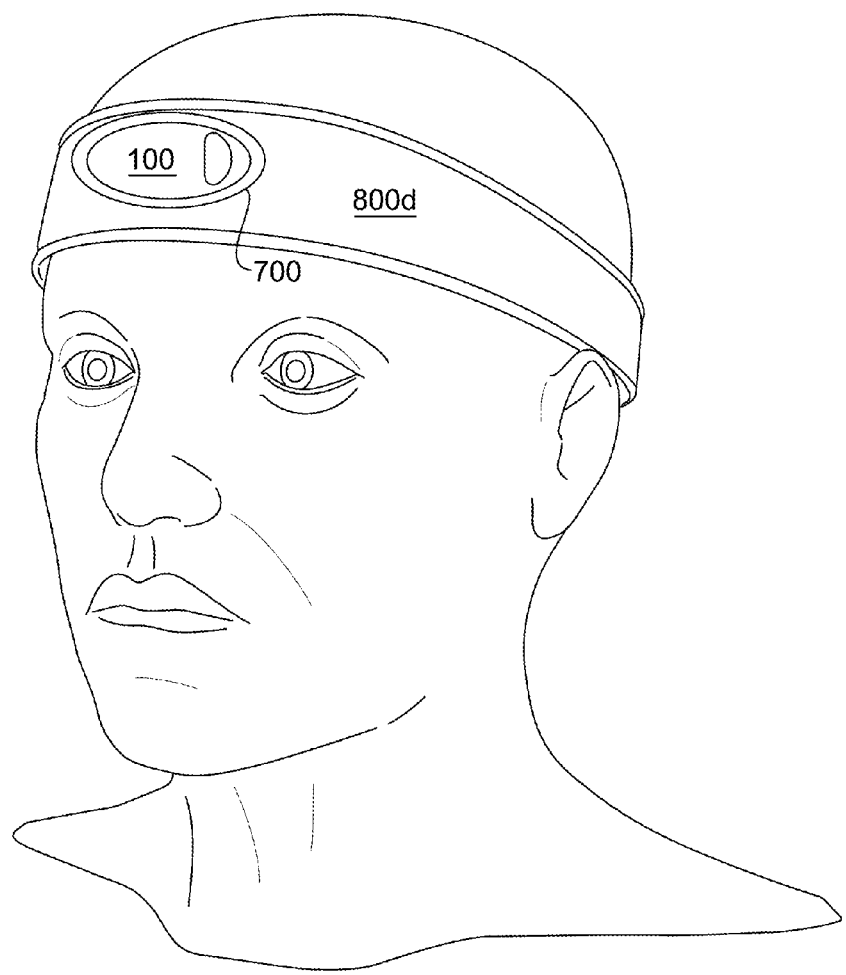
FIG. 8D illustrates the sensor pod, introduced in FIGS. 1A, 1B and 1C, attached to a headband.

FIG. 8D illustrates the sensor pod 100 attached to a headband 800d.

Figure 8E:
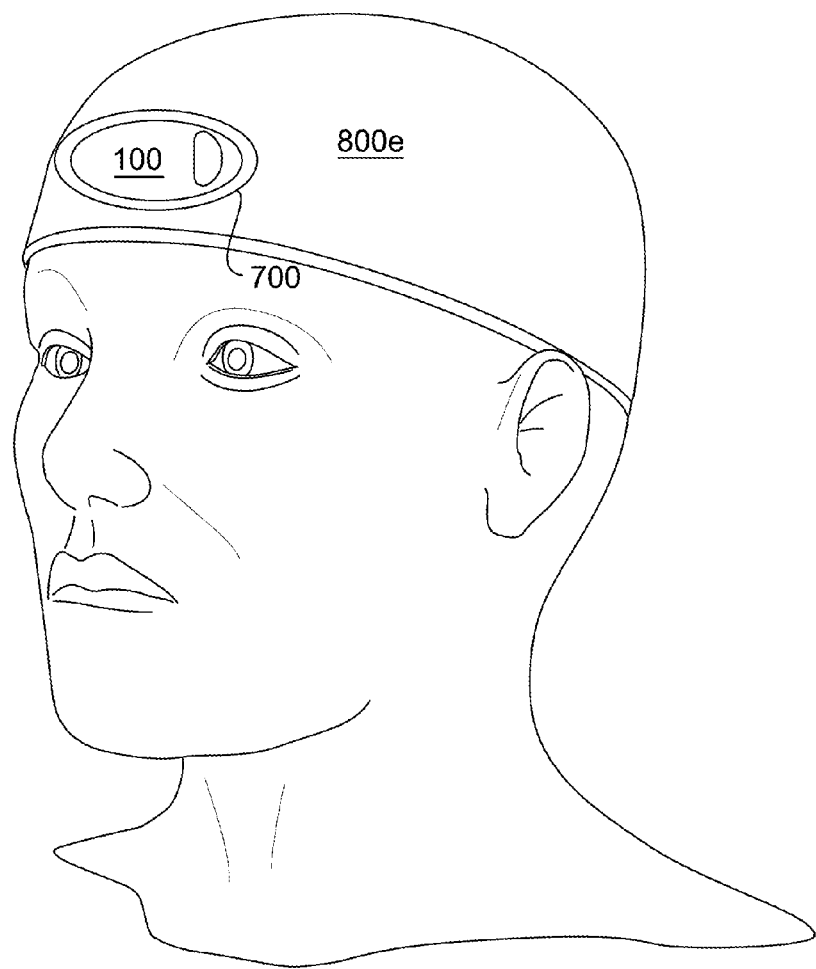
FIG. 8E illustrates the sensor pod, introduced in FIGS. 1A, 1B and 1C, attached to a swim cap.

FIG. 8E illustrates the sensor pod 100 attached to a swim cap 800e.

Figure 9:
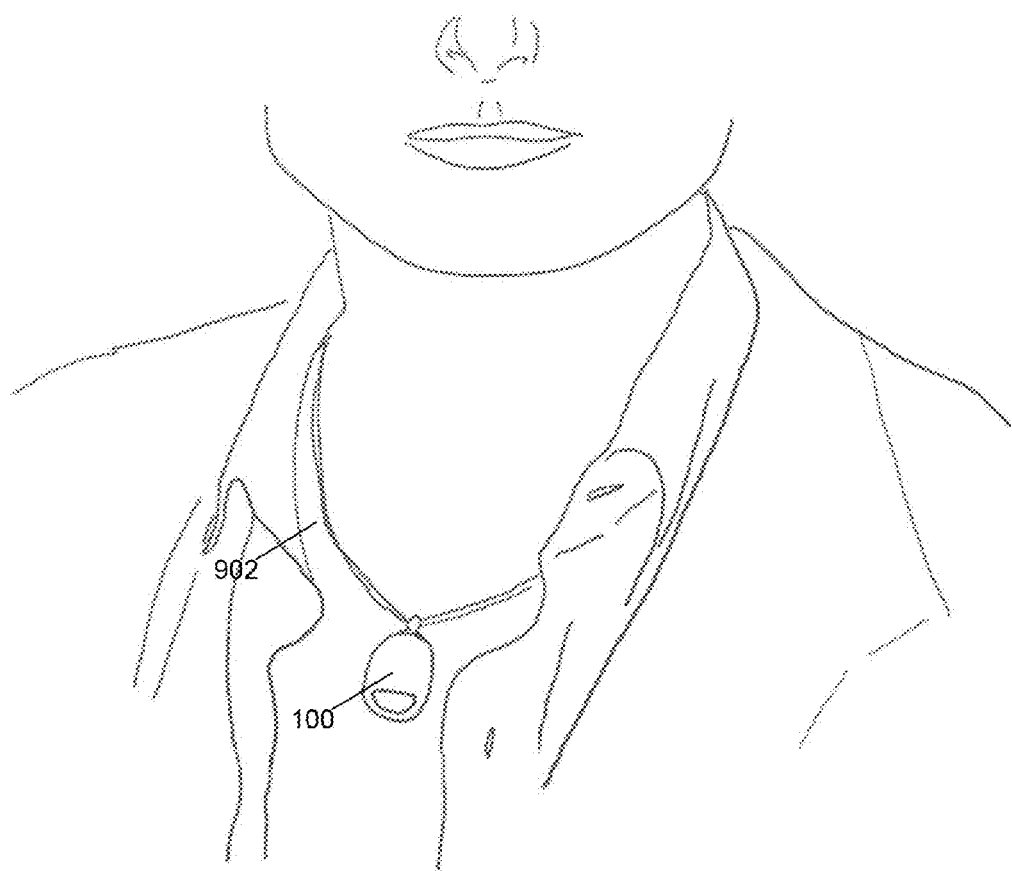
FIG. 9 illustrates the sensor pod, introduced in FIGS. 1A, 1B and 1C, hanging from a necklace in a similar manner that a pendant hangs from a necklace.

FIG. 9 illustrates the sensor pod 100 hanging from a necklace 902, in a similar manner that a pendant hangs from a necklace.

Figure 10:
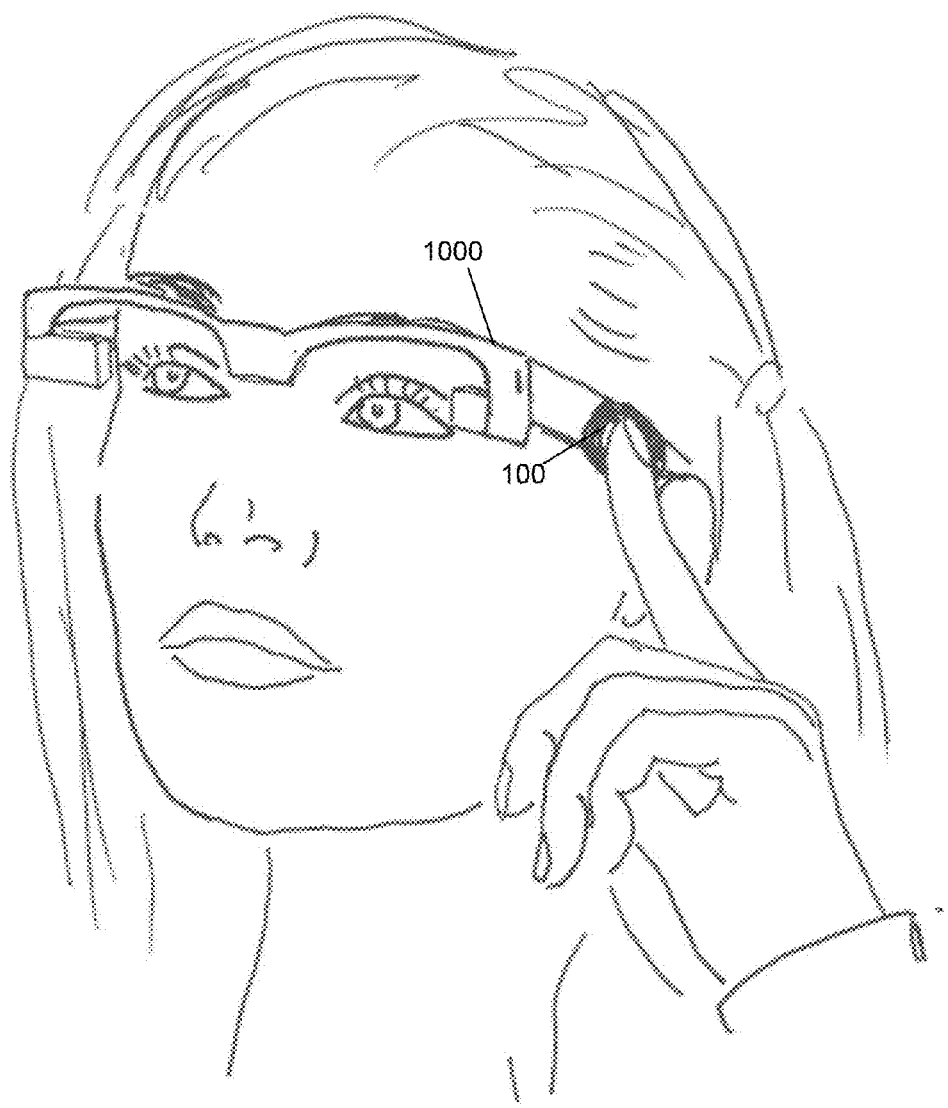
FIG. 10 illustrates the sensor pod, introduced in FIGS. 1A, 1B and 1C, attached to a head mounted display device.

FIG. 10 illustrates the sensor pod 100 attached to a head worn display device 1000. The sensor pod can similarly be attached to other types of glasses.

Figure 11:
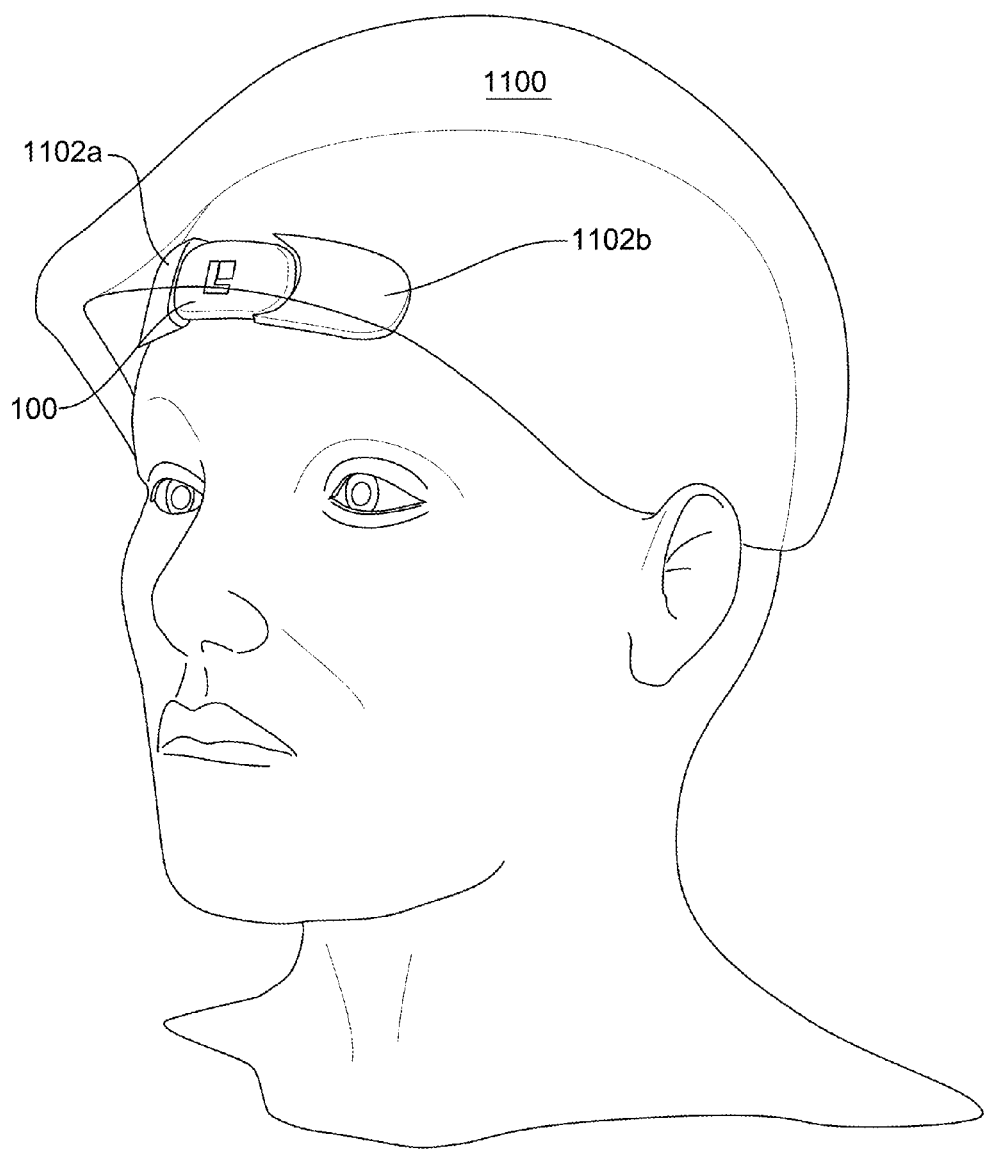
FIG. 11 illustrates the sensor pod, introduced in FIGS. 1A, 1B and 1C, attached to a helmet.

FIG. 11 illustrates the sensor pod 100 attached to a helmet body 1100. The helmet body 1100 is shown as including a pair of connectors 1102a and 1102b attached to a portion of the helmet body 1100 that is intended to rest against a user's forehead. These connectors 1102a and 1102b enable the physiologic sensor pod 100 to be selectively attached to the helmet body 1100. An elastic ring type of connector, the same or similar to the elastic ring 700 described above, can be used in place of the pair of connectors 1102a and 1102b. Other types of connectors that enable the sensor pod 100 to be selectively connected to the helmet body 1100 are also possible and within the scope of the embodiments described herein.

FIG. 12A illustrates a lapel adaptor 1200 that is configured to be selectively attached with or to the sensor pod 100 to enable the sensor pod 100 to be clipped to a lapel, a shirt pocket, a pant pocket, or the like. The lapel adaptor 1200 includes a first portion 1201 that is adapted to be selectively attached to the sensor pod 100, a second portion 1202, and a third portion 1203 between the first and second portions 1201 and 1202. The third portion 1203 is adapted to enable the second portion 1202 to be folded toward the first portion 1201, and vice versa, and thus the third portion 1203 operates as a hinge, and thus, can be referred to as a hinge or a hinged portion 1203. The second portion 1202 includes a pair of magnets 1206a and 1206b that are spaced apart from one another by approximately the same distance that the electrodes 106a and 106b are spaced apart from one another on the bottom surface 114 of the sensor pod 100. In accordance with an embodiment, the entire lapel adaptor 1200, except for the magnets 1206a and 1206b, is made of silicon, rubber, or some other flexible material. In accordance with another embodiment, the first portion 1201 and the third portion 1203 of the lapel adaptor is made of silicon, rubber, or some other flexible material, and the second portion 1202 is made of a more rigid material, such as plastic or aluminum. The magnets 1206a and 1206b can be made of magnetic stainless steel, but are not limited thereto. Other variations are possible and within the scope of embodiments described herein.

The first portion 1201 of the lapel adaptor 1200 includes an elastic ring 1207 having an opening 1204. The elastic ring 1207 is shown as having oval or elliptical shape and generally has the same shape as the circumferential surface 110 of the sensor pod 100. In accordance with an embodiment, an inner circumference of the elastic ring 1207 is slightly smaller than the outer circumference of the groove 112 in the circumferential surface 110 of the sensor pod 100. This enables the groove 112 in the sensor pod 100 to be snapped into the opening 1204 in the elastic ring 1207 and held in place.

FIG. 12B is a perspective view of the lapel adaptor 1200 with the sensor pod 100 snapped into the opening in the elastic ring 1207 of the first portion 1201 of the lapel adaptor 1200. FIG. 12C is a side view of the lapel adaptor 1200 with the sensor pod 100 snapped into the opening in the elastic ring 1207 of the first portion 1201 of the lapel adaptor 1200, with the second portion 1202 folded toward the first portion 1201 such that the magnets 1206a and 1206b are aligned, respectively, with the electrodes 106a and 106b on the bottom surface 114 of the sensor pod 100. In this configuration, the magnet 1206a and the electrode 106a are attracted to one another, and the magnet 1206b and the electrode 106b are similarly attracted to one another. While not shown in FIG. 12C, a portion of a lapel, pocket or other article of apparel or clothing can be positioned between the magnets 1206a and 1206b and the electrodes 106a and 106b. Nevertheless, the magnetic force between the magnets 1206a and 1206b and the electrodes 106a and 106b will maintain the lapel adaptor 1200 in its folded position. The magnets 1206b and 1206a can be permanent magnets. Alternatively, the magnets 1206b and 1206a can include metal segments behind which permanent magnets are located to thereby magnetize the metal segments.

In the FIGS. and the above description, the sensor pod 100 was shown as and described as having an oval or elliptical circumferential shape. In alternative embodiments the sensor pod 100 can have alternative circumferential shapes, such as circular, rectangular, or square, but not limited thereto. Where the sensor pod 100 has an alternative circumferential shape, the elastic rings (e.g., 700 and 1207) described herein, which are used to selectively attached the sensor pod 100 to an article of apparel or clothing, or to an lapel adaptor, can similarly have such an alternative circumferential shape.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto. While various embodiments have been described above, it should be understood that they have been presented by way of example, and not limitation. It will be apparent to persons skilled in the relevant art that various changes in form and detail can be made therein without departing from the spirit and scope of the invention. The breadth and scope of the present invention should not be limited by any of the above-described exemplary embodiments, but should be defined only in accordance with the following claims and their equivalents.

What is claimed is:

1. A lapel adaptor for use with a physiologic sensor pod having a housing including a top surface, a bottom surface, a peripheral surface extending between the top and bottom surfaces, a groove extending around the peripheral surface, and a pair of electrodes spaced apart from one another on the bottom surface of the housing, the lapel adaptor comprising:
   a first portion comprising an elastic ring including an opening having an inner circumference that is slightly smaller than an outer circumference of the groove extending around the peripheral surface of the housing of the physiologic sensor pod;
   a second portion having a pair of magnets spaced apart from one another by substantially a same distance as a distance between the pair of electrodes on the bottom surface of the housing of the physiologic sensor pod; and
   a third portion, between the first and second portions, adapted to enable the first and second portions of the lapel adaptor to be folded toward one another.

2. The lapel adaptor of claim 1, wherein when a said physiologic sensor pod is selectively inserted into the elastic ring, such that a portion of the elastic ring rests within the groove extending around the peripheral surface of the housing of the physiologic sensor pod, and when the first and second portions of the lapel adaptor are folded toward one another, the pair of magnets of the second portion of the lapel adaptor and the pair of electrodes on the bottom surface of the housing of the physiologic sensor pod are attracted toward one another.

3. The lapel adaptor of claim 1, wherein the elastic ring is made of at least one of rubber or silicone.

4. The lapel adaptor of claim 1, wherein the third portion comprises a hinge portion.

5. The lapel adaptor of claim 1, wherein the third portion is made of at least one of rubber and silicone.

6. The lapel adaptor of claim 1, wherein the pair of magnets are made of magnetic stainless steel.

7. The lapel adaptor of claim 1, wherein the third portion is narrower than the second portion.

8. The lapel adaptor of claim 1, wherein the opening in the elastic ring has an oval or elliptical shape.

9. A lapel adaptor for use with a physiologic sensor pod having a housing including a top surface, a bottom surface, a peripheral surface extending between the top and bottom surfaces, a groove extending around the peripheral surface, and a pair of electrodes spaced apart from one another on the bottom surface of the housing, the lapel adaptor comprising:
   an elastic ring including an opening adapted to accept the housing of the physiologic sensor pod;

an elongated portion having a pair of magnets spaced apart from one another; and a hinge portion, between the elastic ring and the elongated portion, adapted to enable the elastic ring and the elongated portion of the lapel adaptor to be folded toward one another.

10. The lapel adaptor of claim 9, wherein the elastic ring has an inner circumference that is slightly smaller than an outer circumference of the groove extending around the peripheral surface of the housing of the physiologic sensor pod.

11. The lapel adaptor of claim 9, wherein the pair of magnets of the elongated portion are separated from one another by substantially a same distance as a distance between the pair of electrodes on the bottom surface of the housing of the physiologic sensor pod.

12. The lapel adaptor of claim 9, wherein when a said physiologic sensor pod is selectively inserted into the elastic ring, such that a portion of the elastic ring rests within the groove extending around the peripheral surface of the housing of the physiologic sensor pod, and when the elastic ring and elongated portion of the lapel adaptor are folded toward one another, the pair of magnets of the elongated portion of the lapel adaptor and the pair of electrodes on the bottom surface of the housing of the physiologic sensor pod are attracted toward one another.

13. The lapel adaptor of claim 9, wherein the pair of magnets are made of magnetic stainless steel.

14. The lapel adaptor of claim 9, wherein the hinge portion is narrower than the elongated portion.

15. The lapel adaptor of claim 9, wherein the opening in the elastic ring has an oval or elliptical shape.

16. An adaptor for use with a physiologic sensor pod, the adaptor comprising:

an elastic ring including an opening having an inner circumference that is slightly smaller than an outer circumference of a groove extending around a peripheral surface of the physiologic sensor pod;

a further portion having a pair of magnets spaced apart from one another by substantially a same distance as a distance between a pair of electrodes on the physiologic sensor pod; and a hinge portion between the elastic ring and the further portion.

17. The adapter of claim 16, wherein the hinge portion enables the elastic ring and the further portion of the adaptor to be folded toward one another.

18. The adaptor of claim 16, wherein the elastic ring is made of at least one of rubber or silicone.

19. The adaptor of claim 16, wherein the pair of magnets are made of magnetic stainless steel.

20. The adaptor of claim 16, wherein the hinge portion is narrower than the further portion.

* * * * *